United States Patent [19]

Mensink et al.

[11] 4,285,345

[45] Aug. 25, 1981

[54] MONOLITHIC PACEMAKER UTILIZING I²L CIRCUITRY

[75] Inventors: Kornelis A. Mensink, Voorst; Hendrik L. Brouwer, Leeuwarden, both of Netherlands

[73] Assignee: Vitatron Medical B.V., Dieren, Netherlands

[21] Appl. No.: 54,019

[22] Filed: Jul. 2, 1979

[51] Int. Cl.³ .............................................. A61N 1/36
[52] U.S. Cl. ........................................... 128/419 PG
[58] Field of Search ................... 128/419 PG, 419 PT

[56] References Cited

U.S. PATENT DOCUMENTS

| | | | |
|---|---|---|---|
| 3,618,615 | 11/1971 | Greatbatch | 128/419 PG |
| 3,631,860 | 1/1972 | Lopin | 128/419 PG |
| 3,718,909 | 2/1973 | Greatbatch | 128/419 PT |
| 3,833,005 | 9/1974 | Wingrove | 128/419 PG |
| 3,920,024 | 11/1975 | Bowers | 128/419 PG |
| 3,945,387 | 3/1976 | Adams | 128/419 PG |
| 3,949,758 | 4/1976 | Jirak | 128/419 PG |
| 4,055,189 | 10/1977 | Averbach et al. | 128/419 PG |

*Primary Examiner*—William E. Kamm
*Attorney, Agent, or Firm*—Woodcock, Washburn, Kurtz, Mackiewicz & Norris

[57] ABSTRACT

A monolithic pacer is provided which utilizes I²L circuitry in combination with linear transistors, providing the conventional advantages of analog circuitry together with the flexibility of digital circuitry. Low current drain operation is achieved by current source control of circuit operating conditions, with I²L gates being utilized alone and in combination with linear transistors to provide current sources. The pacer provides "on-demand" logic and is externally programmable.

23 Claims, 10 Drawing Figures

MONOLITHIC PACEMAKER UTILIZING I²L CIRCUITRY

BACKGROUND OF THE INVENTION

This invention lies in the field of physiological stimulating devices and, more particularly, demand-type cardiac pacemakers adapted for low power operation. The pacemaker of this invention is distinguished by its use of I²L circuitry in low current drain configurations.

Cardiac pacers are today widely known and utilized in many regions of the world. Since the founding of the pacemaker industry, there has been an evolution of a number of different types of pacemakers in terms of the functions performed and also in terms of the technology utilized. To date, most pacemakers have utilized analog circuitry, wherein the linear transistor is the main building block. More recently the pacemaker industry has introduced some "digital" models, utilizing digital circuitry for generating the stimulus pulses and for carrying out various desired pacer functions which have been incorporated in more sophisticated pacemaker designs. Digital circuitry has gained acceptance particularly in the area of programmable pacers. Another non-functional classification of pacemakers involves the particular structure or means of embodiment of the circuitry. Thus, early pacemakers utilized only discrete element design. This has been followed by hybrid models, incorporating integrated circuits together with discrete components. The next step beyond this, to which the industry is turning its attention, is the "monolithic" pacer, wherein virtually all or most all of the circuitry is embodied on a single chip, or several chips.

The analog circuits which have been utilized in past pacemaker designs have a proven reliability and effectiveness. This reliability is, of course, highly desirable for pacemaker devices which must be designed in anticipation of lifetimes of 10 and more years. At the same time, the flexibility of digital circuits has proven itself well, and is particularly adapted for use with programmable pacers where data must be stored and a great many complex logic functions must be carried out. However, the additional complex digital circuitry that is desired is generally achieved only at the cost of greater power consumption. While improved power sources, and the lithium battery in particular, make it possible to handle the power requirements of increased logic circuitry, it remains a fundamental design objective to provide a pacer with the lowest possible overall power consumption. There is thus a fundamental need in the pacemaker art to provide a pacemaker design which incorporates the reliability and effective simplicity of analog circuits in combination with the flexibility of digital circuits, while maintaining very low power operation.

The pacemaker circuit of this invention utilizes a combination of Integrated Injection Logic (I²L) technology in combination with linear transistor circuitry. The disclosed pacemaker is of the monolithic chip type, in that essentially all of the circuitry is provided on one chip which includes the I²L gates, the linear transistors and most of the resistors. High value resistors and capacitors cannot be provided on the chip. A typical chip is made up of different sections, or regions, including a region devoted to an array of quad-output I²L gates and a region comprised of bipolar NPN and PNP transistors as well as resistors. In the drawings presented with this specification, the conventional designations of multiple collector linear transistors and I²L gates are used. Reference is made to the technical literature dealing with I²L technology and designs. This literature provides extensive disclosures of the basic I²L gate, operating characteristics of I²L gates, I²L logic design, and the general utilization of chips using I²L.

SUMMARY OF THE INVENTION

It is an object of the invention to provide a pacemaker utilizing I²L and linear transistor technology, which pacemaker achieves reliable low power operation and has the capability of responding to external programming signals.

It is another object of this invention to provide a low power pacemaker incorporating current source control of a variety of pacemaker parameters, including oscillator rate, hysteresis rate, amplifier sensitivity and testing for pacer threshold.

It is another object of this invention to provide a pacemaker utilizing I²L technology, wherein I²L current sources are employed to stabilize a plurality of circuit switching levels.

It is another object of this invention to provide improved current control circuits particularly adapted for use in low current applications. The current control circuits utilize an I²L gate with at least one collector in a feedback connection to the base, thereby controlling the current capacity of the other collectors. The I²L gate may be connected in series with a linear transistor and/or a multiple collector transistor having at least one collector in a feedback connection to its base.

It is another object of this invention to provide an I²L source/sink connected to the input of a switching device such as a transistor or equivalent, thereby providing a controlled threshold switching circuit.

It is another object of this invention to provide a pacemaker using I²L technology, wherein the combination of an I²L gate and linear transistor is used to provide current source control of one or more circuits.

It is another object of this invention to provide a pacemaker having current source control of a plurality of pacemaker parameters, wherein the current source control is provided by an I²L gate circuit in combination with a multiple collector linear transistor.

It is another object of this invention to provide a pacemaker having an amplifier adapted to be connected to receive heartbeat signals from the heart, which amplifier includes current source control of the amplifier sensitivity. The amplifier is designed to provide an on-off output, responding to input signals above a given threshold, and employs a current sink circuit connected to its output to prevent switching of the output except when the input signal exceeds the predetermined threshold value. The amplifier circuit utilizes a current mirror configuration for driving both the input and output paths.

It is another object of this invention to provide a pacemaker having current source control of at least one circuit portion, the current source control being provided by at least one I²L gate having at least one collector tied in feedback relation to its input, the other I²L collectors being connected through a linear transistor to a multiple collector transistor, wherein the injector current provided to the I²L gate controls the output current source capacity of the multiple collector transistor.

It is another object of this invention to provide a pacemaker having circuitry utilizing differences in forward voltage drops of at least two transistors, I²L gates or diodes, being different in geometry and/or diffusion parameters, in order to create a current-mirror configuration with a predetermined ratio between applied current and generated current.

It is another object of this invention to provide a pacemaker with means for adjusting the rate of delivery of stimulus pulses to one of a plurality of operating rates, comprising a controllable current generator circuit in combination with an oscillator, the oscillator being adapted to operate at a rate determined by the current provided by the controllable current generator. The current generator circuit further comprises means for adjusting the rate current source in response to receipt of an external programming signal, and more particularly comprises an I²L gate which is connected to receive injector current upon detection of an external program signal. The current generator circuit suitably comprises a plurality of current generators which are switched into and out of operation in response to received signals.

It is another object of this invention to provide a pacemaker having an oscillator for providing timing signals from which stimulus pulses are derived, the oscillator having a pair of multiple collector transistors in current mirror configuration, selected collectors of each of the transistors being connected to provide current to charge a capacitor, the duty cycle being a function of such collector selection. The oscillator rate is determined by the driving current provided by the current mirror configuration, which in turn is controlled by a rate current provided by a separately controlled current source. An I²L gate flip-flop is utilized in connection with the current mirror configuration to control switching of the oscillator. Operation of the entire oscillator is under the control of a current source comprising an I²L gate circuit in combination with a linear transistor.

It is another object of this invention to provide a pacemaker having circuitry for generating periodic stimulus pulses at one of a plurality of pulse rates, and comprising a high rate limiter circuit for preventing delivery of stimulus pulses at a rate above a predetermined limit, said limiter circuit comprising I²L and linear transistor components. The high rate limiter comprises an I²L set/reset flip-flop which is maintained in a "limiting" state when stimulus signals are generated at an excessive rate. In the limiting state, delivery of stimulus pulses is maintained at a rate below the high rate limit.

It is another object of this invention to provide a cardiac pacemaker for delivering stimulus pulses, the pacemaker comprising a pulse width circuit for fixing the width of said stimulation pulses at a predetermined width, said pulse width circuit comprising a double thyristor switching circuit for providing sharp leading and trailing edges. The switching circuit is low current triggered and delivers a relatively high constant current output pulse substantially independent of source voltage.

It is another object of this invention to provide a pacemaker adapted to be programmed, either to change an operating variable or to carry out a test such as searching for threshold, the pacemaker comprising a marker generator for generating a marker pulse of predetermined level and width, and timed to indicate receipt of the program. The marker generator comprises I²L gates which are normally de-energized, i.e., do not receive injector current, but which are energized upon receipt of an external programming signal. The marker signal is generated only after a predetermined time delay following decoding of a properly transmitted external program signal, and is timed to occur in a predetermined time relationship with the previous delivered stimulus pulse.

It is another object of this invention to provide a pacemaker utilizing I²L circuits, and comprising an injector current circuit having a first injector rail which is continuously connected to provide injector current to a first group of I²L gates and at least a second injector rail which is normally de-energized but which is energized upon receipt of an external programming signal. The second injector rail is connected to the first injector rail in a follower arrangement, voltage or current, whereby plural injector rails are provided which provide substantially the same injector current to all I²L gates, regardless of the total injector current load for all circuits.

It is another object of this invention to provide a pacemaker for delivering stimulus pulses to a patient's heart, the pacemaker having a program circuit for receiving and decoding external program signals and a threshold test circuit for carrying out a test to determine the patient's threshold to delivered stimulus pulses, the threshold test circuit being controlled by signals from the program circuit. The threshold test circuit operates in combination with a plurality of controllable current sources which provide control currents for providing programmed output levels. The threshold test circuit contains I²L gates which are normally de-energized and which are energized only when an external programming signal is received.

It is another object of this invention to provide a programmable pacemaker adapted to receive external program signals and store data derived therefrom in a multiple stage resistor. The multiple stage register drives a plurality of I²L gate digital to analog converter circuits, each of such circuits providing a predetermined current sink. The digital to analog circuit arrangement is connected to and is operatively in combination with current-controlled circuit means, whereby at least one operating parameter of such circuit means is controlled in accordance with the externally received program. More specifically, for the digital to analog converter arrangement of this invention, there are utilized a plurality of I²L gate sink circuits, each controllable from the register to an on-off state, the gate sink circuits having different collector arrangements to provide different current sink values.

In accordance with the above, there is provided a pacemaker utilizing I²L and linear transistor technology, which pacemakers provides the logic functions required for a demand pacer and also incorporates external programming capability for carrying out a threshold test. Specific circuits which embody the objects as set forth hereinabove are incorporated to provide a pacemaker having the reliability of conventional bipolar technology together with the flexibility of digital circuit technology, the entire pacer circuit operating at very low power drain.

DESCRIPTION OF THE PREFERRED EMBODIMENTS

Figure 1:
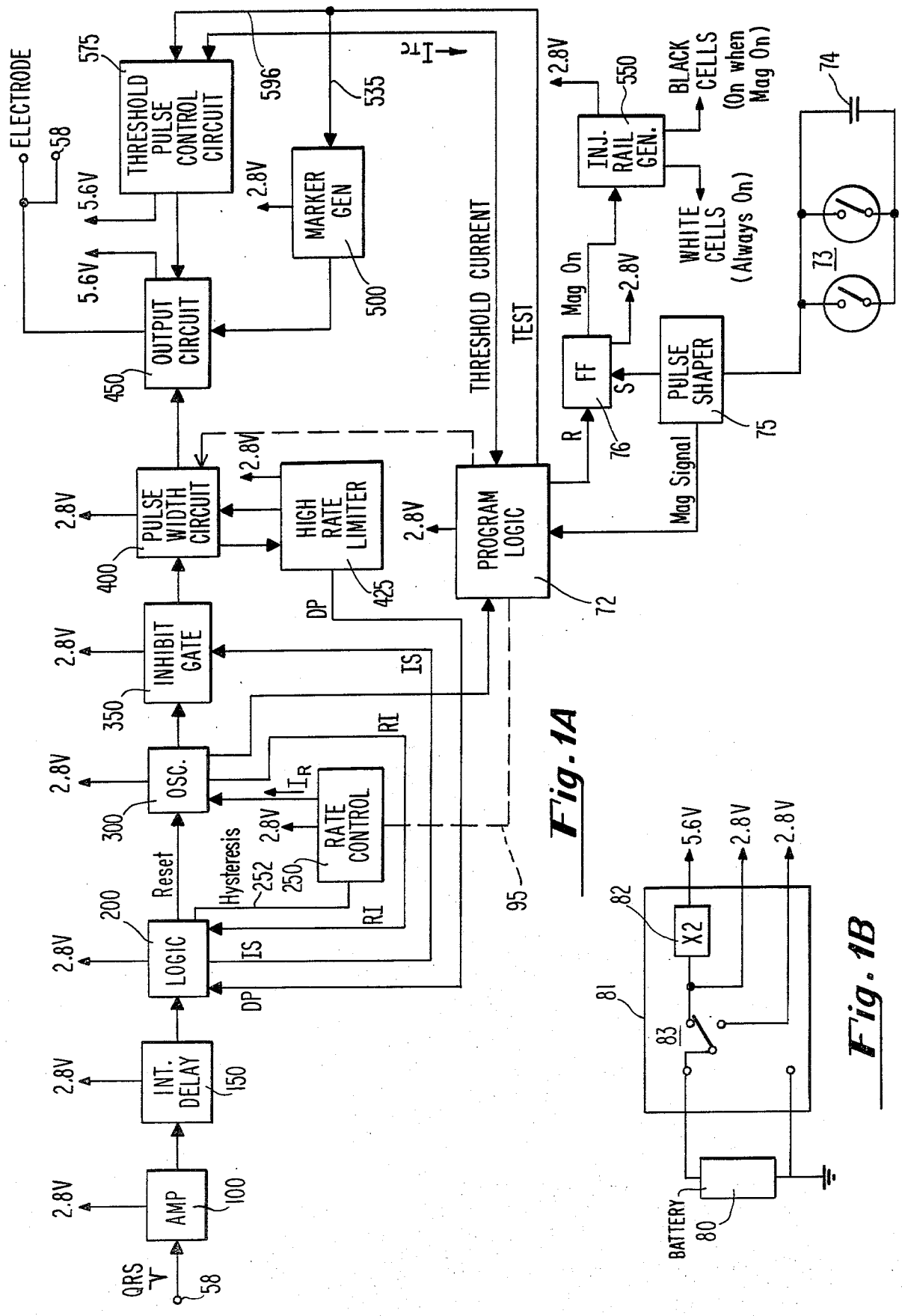
FIG. 1A is a block diagram of the overall pacer of this invention.
FIG. 1B is a diagram of the switching converter type of power supply circuit used in providing power to the pacer circuits.

Referring to FIG. 1A, there is shown a block diagram of the overall pacer. The illustrated pacer is a demand, or ventricular-inhibited pacer, with means for providing hysteresis whereby the escape interval during inhibited operation corresponds to a lower rate. The pacer is also programmable, having a program logic portion 72 which is activated by an externally applied magnetic signal. In the embodiment as shown, the program logic provides for the carrying out of a threshold test, whereby the pacer goes into fixed rate 95 bpm on demand operation, and the output pulse is dropped in increments of 0.5 volts so that the doctor can determine the level at which the stimulus fails to capture, thereby determining the patient threshold. Other pacer parameters, such as rate and pulse width may be likewise changed by an external programming circuit, in accordance with techniques well known in the art. Reference is made to U.S. Pat. No. 4,124,031, assigned to the same assignee, for a disclosure of a pacer with a specific logic circuit diagram for changing selected pacer operating parameters. Such application is incorporated by reference for the purpose of showing a typical logic circuit for receiving external magnetic signals, detecting a predetermined coding of such signals, and changing one or more pacer operating parameters in accordance with such detected coded signals.

When the pacer of this invention is free running, i.e., not inhibited, oscillator 300 provides timing signals which are connected through gate 350 to pulse width circuit 400, which generates a pulse width of a predetermined time period. The output of pulse width circuit 400 is connected to output circuit 450 which provides output stimulus pulses of the determined pulse width. The stimulus pulses are outputted to an electrode adapted to be placed in contact with the patient's heart, in accordance with well known techniques. The electrode is also connected to terminal 58 which is the input terminal of amplifier 100. Amplifier 100 has a threshold level which is either fixed or adjustable, and generates an output response upon input of a QRS signal exceeding such threshold level. The output from amplifier 100 is connected to interference delay circuit 150, which blocks passage of unwanted interference. As is described in detail hereinafter, delay circuit 150 comprises a timeout circuit which effectively blocks passage of succeeding signals which come along within a time period shorter than a predetermined time period. The output of delay circuit 150 is connected to the on-demand logic circuit 200, which performs a variety of logic functions necessary to coordinate the operation of the demand pacer. For normal on-demand operation, circuit 200 provides a reset pulse following a received natural QRS signal, which reset pulse is connected to oscillator 300 and causes it to reset its timing cycle. At the same time, logic circuit 200 provides an Inhibit Signal (IS) which is connected to inhibit gate 350, which gate inhibits connection of an output from oscillator 300 to the pulse width circuit 400 whenever the oscillator has been reset by a natural QRS signal. By this means, outputs from oscillator 300 cause delivered stimulus pulses only following timing out of the oscillator, such that no pulses are delivered following detection of a natural QRS signal. The resetting or timing out of oscillator 300 produces a Refractory Inverse signal (RI), which is connected to logic circuit 200 to prevent oscillator reset due to any signal detected at node 58 for a predetermined refractory interval following timeout of the oscillator.

Rate control circuit 250 is shown providing an output current designated $I_R$ to oscillator 300. Oscillator 300 has a linear timing circuit adapted so that the timing interval is set and controlled by the current $I_R$. For normal operation at about 70 bpm, $I_R$ is set at a first value. When the pacer is operating in the inhibited mode, a hysteresis signal is conducted on line 252 to the rate control circuit, causing a change in $I_R$ to correspond to a longer pacer escape interval, i.e., a lower oscillator rate. In the embodiment as described herein in detail, rate control circuit 250 also provides a third value of $I_R$ corresponding to the threshold test mode of operation, at which time the oscillator is set at 95 bpm. Further, if desired, the oscillator rate can be programmed by varying $I_R$ in accordance with program signals connected on line 95 from program logic circuit 72 to rate control circuit 250. Any variety of rate control can be achieved by using the types of control circuits illustrated hereinbelow in connection with the discussion of circuit 250.

High rate limiter circuit 425 is shown connected to pulse width circuit 400. This circuit receives output signals from the pulse width circuit, and if a succeeding output signal arrives within a time period shorter than a predetermined time period, the high rate limiter acts to disable the transmission of a trigger signal from circuit 400 to output circuit 450. The high rate limiter circuit also provides a delivered pulse (DP) signal to the logic circuit, which is used to take the pacer out of hysteresis and to prevent double triggering.

Block 72, designated program logic, receives externally generated and decoded magnetic signals and generates program control signals in response thereto. Two reed switches 73, placed at right angles and shunted by an interference filter capacitor 74, provide on-off signals to pulse shaper 75 corresponding to whether the external magnet signal is present or absent. Pulse shaper 75 provides a sharp on-off magnetic signal to program logic circuit 72. It also provides a set signal (S), at the time of the detection of a magnetic signal, to flip-flop 76, which when set provides a MAG on signal to injector rail generator 71. Injector rail generator 550 provides 2 injector rails for supplying injector current to the I²L gates as used in the circuit of this design. A first rail, indicated as going to the white cells (as shown in the drawings) is always on, providing a current of predetermined value, to be shared by all the gates. In response to the MAG ON signal, generator 550 also provides a current to the black cells (as shown in the drawings). In the arrangement of this invention, this signal goes on when the magnet is first applied, and stays on until the magnet has been removed for at least three patient beats, either pacer-generated or natural, as sensed at electrode node 58.

The program logic circuitry 72 is designed to produce the desired control signals in resonse to the received magnetic signal. The external magnetic or equivalent signal may be of any predetermined coded form which is suitable for reliable and secure detection. For the pacer as here disclosed, only one logic function, or sequence, is illustrated as performed by program logic block 72, namely the threshold test, although any number of like programming functions may be employed. The key required to place the pacer in the threshold test mode, for purposes of illustration, is as follows:

(1) The magnet is applied to close switches 73 for a time period embracing at least four heartbeats;

(2) The magnet is removed, thus opening switches 73, for a period less than two heartbeats;

(3) The magnet is reapplied for a period less than two heartbeats;

(4) The magnet is removed again for a period less than three heartbeats;

(5) The magnet is reapplied. The test starts after the magnet has been applied for four heartbeats, but is stopped whenever the magnet is removed.

Program logic circuit 72 contains logic elements, similar to those illustrated in U.S. Pat. No. 4,124,031, for determining when the above coded program, or "key" has been properly entered. When it has been entered, program logic circuit 72 produces a test signal which is connected on line 535 to marker generator 500. In the illustrated embodiment, marker generator 500 produces, following a 50 ms delay after the start of test, a current controlled marker pulse of 1 ma, which is outputted through output circuit 450 to the electrode. Since, for the code illustrated, the test is initiated upon counting the fourth stimulus pulse following the last application of the magnet, the marker generator occurs 50 or 100 ms following a stimulus pulse, and consequently is safely positioned with respect to the patient's T-wave. The purpose of generating this marker is to permit the examining physician to know precisely when the test has started, so that he can begin to count the patient's pulses (which step is necessary in order to determine the patients threshold). Since the 1 ma pulse is a reference pulse, and lasts for a predetermined 2 ms, it is easily discernible by the doctor. Alternately, the marker generator is designed to produce a pulse about 150 ms after the refractory period (about 400 ms following the prior stimulus pulse instead of 50 ms). In this second embodiment the marker is used to recycle the pacer and cause a rhythm gap on the ECG trace which shows clearly where the test begins.

The test signal is also connected, at line 596, to the threshold pulse control circuit 575, which controls output circuit 450 during the test. Threshold pulse control circuit 575 effectively takes over control of amplitude and causes the output circuit 450 to deliver output pulses in accordance with a predetermined program. For the preferred embodiment, during the threshold test program the output circuit provides a series of 4 pulses at a first voltage level, then drops in amplitude 0.5 volts and delivers another 4 pulses, and continues in this manner until it reaches 0.5 v (after which it returns to full output) or the magnet is removed by the doctor at loss of patient capture. The doctor knows the value of the last pulse which achieves capture since he has counted the heartbeats since the start of test (when the marker signal is seen). At loss of capture, the doctor removes the magnet, which immediately takes the pacer out of the threshold program and resets all circuitry to the normal demand mode of operation.

Referring to FIG. 1B, there is shown a block diagram of the circuitry utilized for supplying power to different circuit portions of the pacer of this invention. The battery source 80 is preferably a lithium type battery, which is coupled to a switching converter 81 as described in U.S. Pat. No. 4,031,899, assigned to the same assignee. This circuit incorporates a switch 83 which switches periodically to connect the source 80 to a first path which contains a converter, or multiplier 82 which provides a 5.6 volt output. As indicated in the drawing, a 2.8 volt output is also obtained from a point prior to the converter. A second path, which is connected alternately to the battery, and which is thus isolated from the converter path, also supplies power at 2.8 volts. The advantages of this circuit are set forth in the referenced patent.

AMPLIFIER

Figure 2:
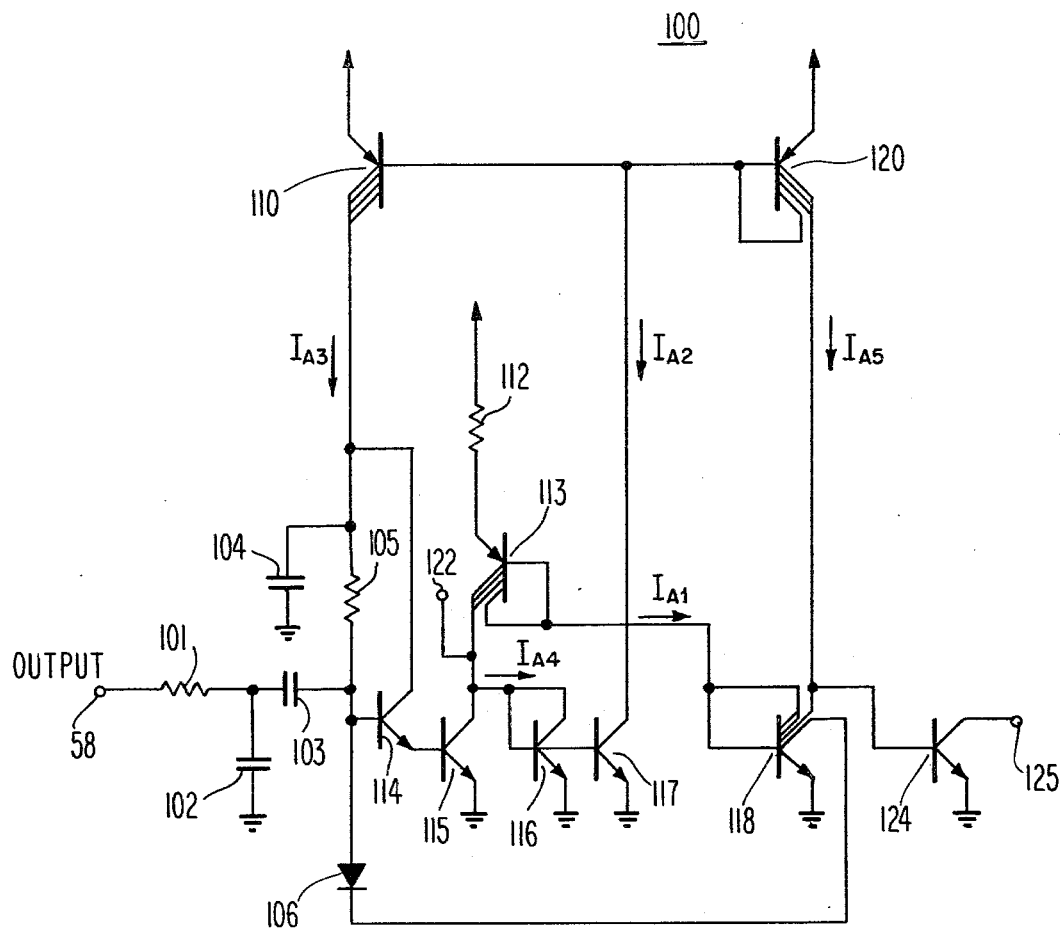
FIG. 2 is a circuit diagram of the amplifier (100) of this invention.

The amplifier 100 is illustrated in FIG. 2. The input signal, applied at node 58, is filtered and connected to the input of Darlington transistor pair 114, 115. Since the collector of 115 is connected to a current source, the input signal causes a variation in current $I_{A4}$, which current is mirrored at $I_{A2}$ through the action of mirror circuit 116, 117. The change in $I_{A2}$ is reflected in a change in current $I_{A5}$ which is connected to one collector of transistor 118 and also to the base of transistor 124. Transistor 118 normally sinks all of current $I_{A5}$, due to the level of fixed current $I_{A1}$, in which condition there is no current into the base of transistor 124 and it is held off. However, when the negative input signal exceeds the predetermined threshold level the resulting variation in $I_{A5}$ causes it to exceed the sink capacity of 118, such that transistor 124 is driven into conduction. Thus, a QRS signal which exceeds the amplifier threshold (i.e., sensitivity) causes a switch in the state of output transistor 124, causing a switch in logic level at node 125.

Examining the detail of the amplifier circuit, amplifier input terminal 58 is connected to a high frequency cutoff filter comprising resistor 101 and capacitor 102, and is coupled through coupling capacitor 103 to the junction of resistor 105, diode 106 and the base terminal of transistor 114. The RC combination comprising capacitor 104 and resistor 105 combines with the combination of 102, 103 in providing desired low signal cutoff characteristics. The junction of capacitor 104 and resistor 105 is connected to the collector of transistor 114 and also to the four collectors of transistor 110.

Resistor 112 in combination with transistor 113 provides an effective current source of approximately a total of 0.4 uA from the four collectors of transistor 113, such that $I_{A1}$ from the single collector is on the order of 100 nanoamps (nA). The 300 nA from the other 3 collectors divides between a first portion that goes into the collector of transistor 115 and a second portion designated as $I_{A4}$ which goes into the collector of transistor 116. Transistor 116 is in a current mirror arrangement with transistor 117, the collector current of which is designated as $I_{A2}$.

The current $I_{A1}$ (about 100 nA) is fed into two collectors of transistor 118, which are tied to the base of that transistor, limiting the current flow in each of the four collectors of transistor 118 to about 50 nA. Thus, the current $I_{A5}$ which flows from the 3 collectors of transistor 120 can be sinked into the one collector of transistor 118 as long as it does not exceed 50 nA. At the same time, the fourth collector of transistor 118, which is connected through diode 106 and resistor 105 to transistor 110 is limited to 50 nA, setting $I_{A3}$ at approximately 50 nA. However, transistor 110 and 120 are in current mirror arrangement so that the total collector current of the 4 collectors of transistor 120 is therefore limited to 50 nA. Since each collector carries about the same current, $I_{A2}$ is accordingly set at 12.5 nA, and $I_{A5}$ is set at 37.5 nA, which is less than the sink capacity of transistor 118. Therefore, under normal conditions no current branches into the base of transistor 124 and it remains off, presenting a logic 1, or high signal at its output.

In order to further appreciate the manner of amplification of the circuit, assume a 1 mv negative going signal at the input, representative of the QRS signal. This signal appears at the input to the Darlington combination of transistors 114 and 115. The $g_n$ of each of these transistors, for the illustrated currents, is about 12 nA/mv, such that the $g_n$ for the combination is about 6 nA/mv. Accordingly, the 1 mv change at the input causes a decrease of 6 nA into the collector of 115 and an increase of 6 nA at current $I_{A4}$ (due to the fixed current coming from the source 112, 113), increasing it from about 12.5 to 18.5 nA. Since transistors 116 and 117 are tied in a current mirror relation, $I_{A2}$ likewise is caused to increase by about 6 nA, in turn causing $I_{A5}$ to increase by 3 times that amount, or about 18 nA. This increase in $I_{A5}$ raises it to about 53.5 nA, which is in excess of the 50 nA which can be sinked into transistor 118. There is thus excess current available which is shunted through the base of transistor 124, which turns it on, producing a change in the signal level at the collector output 125 of transistor 124 (from a logic 1 to a logic 0).

In the use of this amplifier in a pacer, the threshold could be set to be in excess of the T-wave signal. The threshold, i.e., the signal level above which the presence of the signal is detected, is set primarily by the ratio of the number of collectors of transistors 110 and 120 which are tied together. The amplification, as well as the frequency characteristics, may be set by adjustment of resistor 112, which sets the current levels flowing in the circuit. The amplifier sensitivity may be adjusted by connecting an adjustable pot between node 122 and V+. Also, combination 112, 113 may be replaced with a programmable current source for programmed control. The amplifier is effectively insensitive to supply voltage variations, since the values of $I_{A5}$ and $I_{A1}$ would be affected proportionately by any change in the supply voltage. All of the transistors shown in this circuit operate in a linear fashion, i.e., there is no injector current utilized. The current levels here stated by way of example are illustrative only, and may be varied as a matter of design choice. The current values adopted affect the filter characteristics of the amplifier.

It is noted that the circuit of FIG. 2 comprises a first amplifier portion and a second comparator portion. Both these portions are controlled together, i.e., the bias current sets the amplification level and also the comparator threshold. Since both amplification and threshold change together, overall circuit sensitivity changes very little with power supply variations.

It is to be noted that certain components of the amplifier circuit can be replaced with equivalents, within the scope of the invention. For example, transistor 118 may be replaced by an equivalent current sink consisting of a pair of I²L gates, each having at least one collector tied to its base. The fixed current $I_{A1}$ from transistor 113 is used as the injector current, half going to each gate. One collector of each gate is suitably tied to the base of transistor 124, while another collector of each gate is tied back to diode 106.

INTERFERENCE DELAY CIRCUIT

Figure 3:
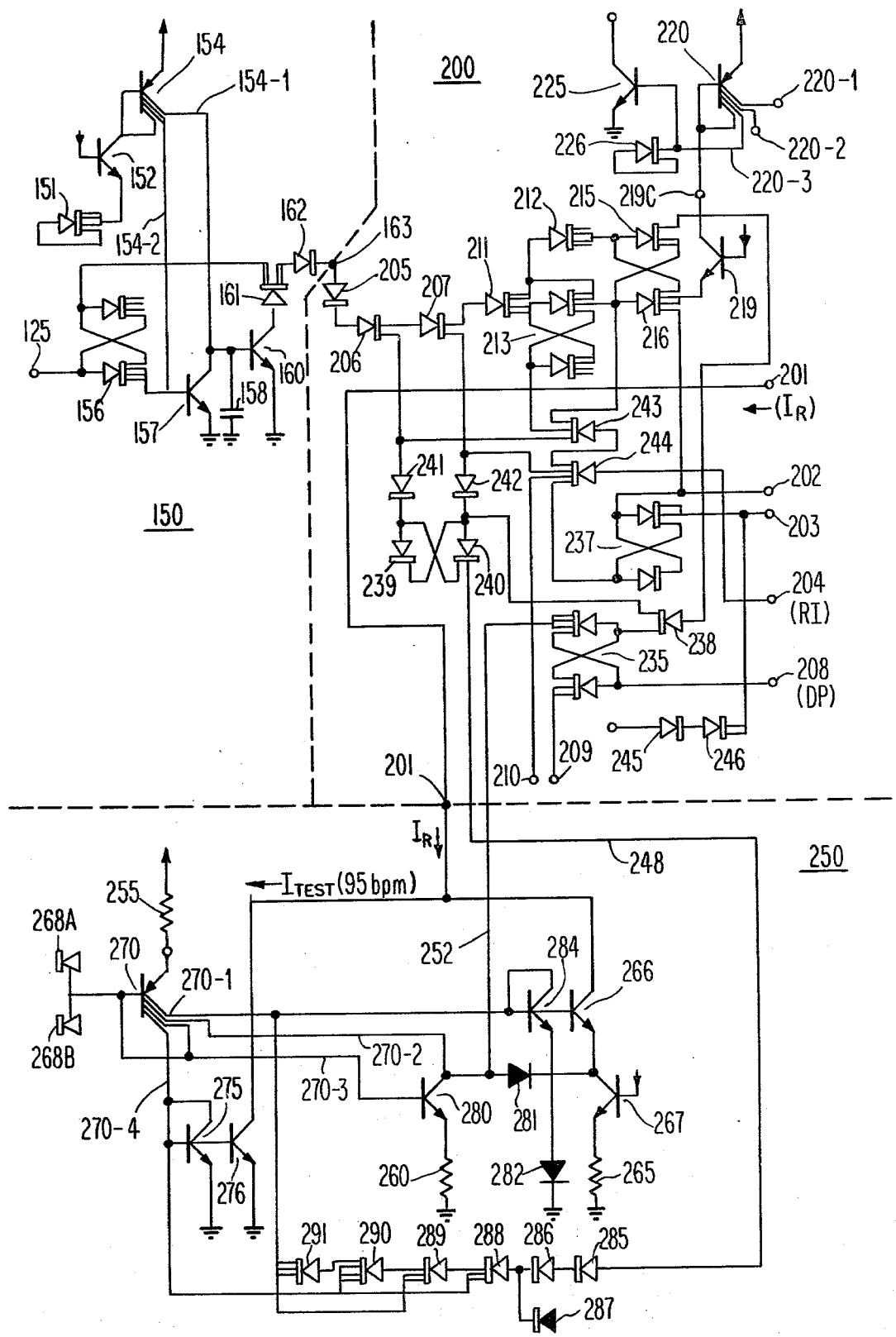
FIG. 3 is a circuit diagram of the interference discriminator (150), logic circuit (200) and rate determining circuit (250) of this invention.

The interference delay circuit 150 is shown in FIG. 3. The pulse signal from amplifier 100 is presented as a negative going signal, i.e., from a logic 1 to a logic 0, at terminal 125 which is connected to the input of flip-flop 156. The output of the flip-flop is connected to the base of transistor 157, the collector of which is coupled to capacitor 158 and the base of transistor 160. I²L gates 161 and 162 provide 2 inversions of the signal before the output which appears at node 163. The output signal at node 163 goes from 0 level to a 1 level whenever the signal at node 125 goes to a zero level, providing a positive going pulse representative of the detection of a QRS signal.

The resettable feature of the interference delay circuit is provided by the charging of capacitor 158 by a current source provided by elements 151, 152, 154. I²L gate 151 has one collector tied to its base, so that its other 3 collectors sink about 30 na. These 3 collectors are tied to the emitter of npn transistor 152, whose collector is tied to the base and one collector of pnp transistor 154. This arrangement causes each collector of transistor 154 to carry 30 na, so that about 30 nA is provided on line 154-1 and about 60 nA on line 154-2. The value of capacitor 158 is chosen to recharge due to the 30 nA current within a preset period to the point of causing transistor 160 to go back into conduction.

In operation, the negative going signal from the amplifier causes switching of flip-flop 156, such that the base of the transistor 157 goes from a 0 to a 1 level, placing that transistor into conduction. When this happens, capacitor 158 is essentially shorted and discharges to a 0 level, thereby turning off transistor 160. This causes the logic level at the input of I²L gate 161 to go from 0 to 1, and the output to go from 1 to 0. This output is fed back to reset flip-flop 156. Gate 162 provides another inversion, such that the output of the delay circuit 150 goes from a 0 level to a 1 level. Following discharge of capacitor 158 and the resetting of flip-flop 156, transistor 157 is again non-conducting, and capacitor 158 starts to be recharged by the 30 nA current flowing on line 154-1. If no new input is received at node 125, capacitor 158 recharges to the point where transistor 160 again conducts, causing the delay circuit output to revert to the 0 logic level. However, if, before this happens, another signal is received from the amplifier, transistor 157 is again made conducting, whereupon capacitor 158 simply discharges again, meaning that it has to time out all over again before the output of the delay circuit reverts to the 0 level. Thus, when any signal comes through within the established time period (e.g. 100 ms), the circuit output stays at a logic 1 level. As long as the interference is present the circuit is continuously reset and does not time out. Note that only the first QRS signal is acted upon, and the unwanted high frequency interference does not reset the oscillator.

ON-DEMAND LOGIC CIRCUITRY

Figure 4:
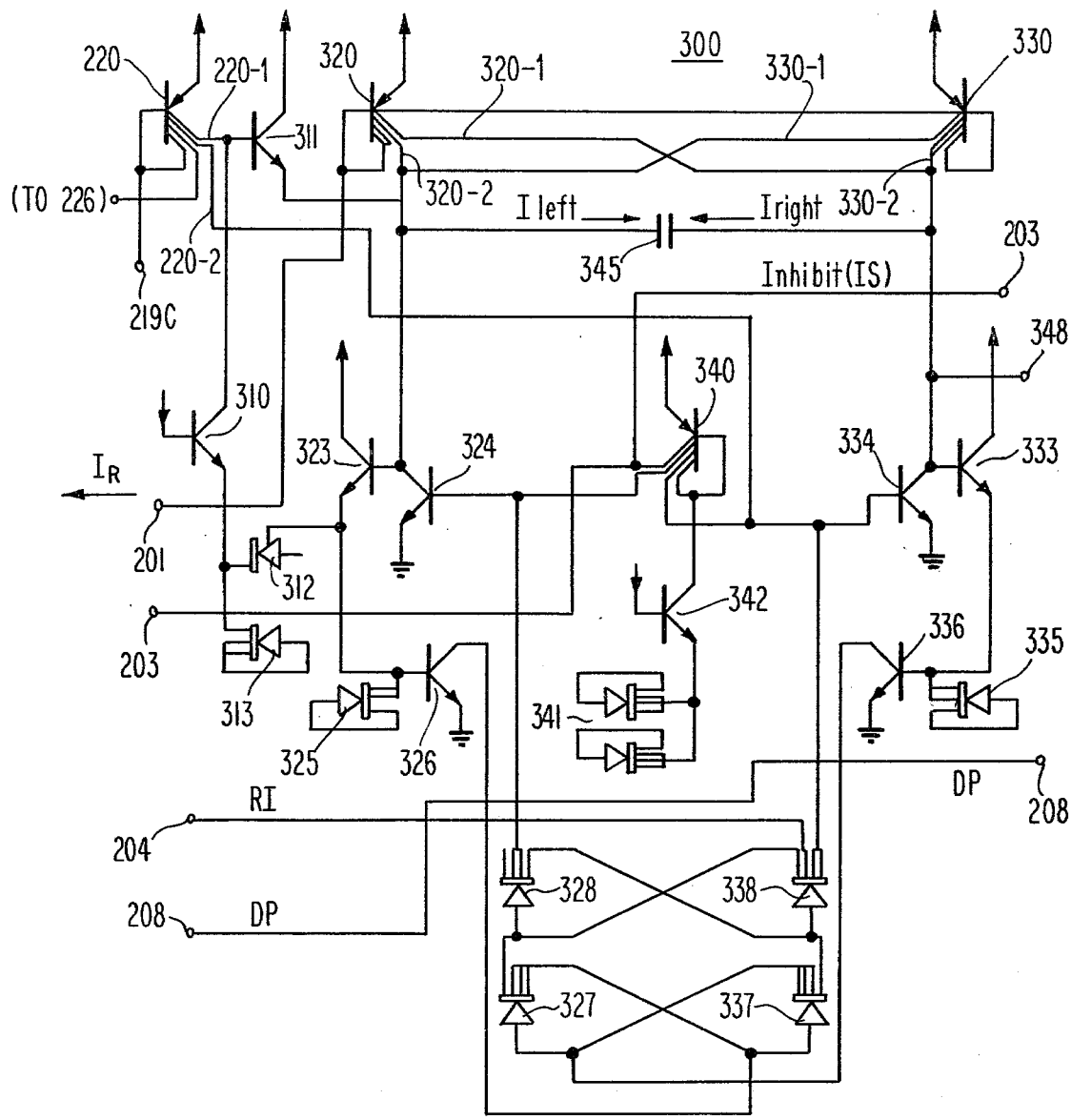
FIG. 4 is a circuit diagram of the oscillator (300) of this invention.

Logic circuitry 200 is contained within the circuitry illustrated in FIG. 3. The output from the interference circuit, which is provided from gate 162 at node 163, is one of the input signals to the logic circuitry. When a QRS signal is detected outside of the refractory interval, the logic circuitry provides an output signal which gates on transistor 220, which (as is seen in FIG. 4) causes resetting of the oscillator. A second input to logic circuit 200 is the Refractory Inverse (RI) signal received from the oscillator 300 at node 204, which signal is normally at a logic 1 level but which goes to a logic 0 level during a refractory period following a detected natural QRS or a delivered stimulus pulse. Following the refractory interval, the RI signal returns to a logic 1 level. A third input to circuit 200 is the Delivered Pulse (DP) signal received at node 208 from the high rate limiter circuit. Upon delivery of an output stimulus pulse, this line goes from a logic 1 to a logic 0 for at least the duration of the output pulse, and then returns to a logic 1 level. It is utilized, as is seen in connection with circuit 250, for controlling whether the oscillator operates at a normal rate or a hysteresis rate (when in the inhibited mode following detection of a natural QRS). A fourth input to circuit 200 is received at node 202, also from the high rate limiter. This input inhibits double triggering of the oscillator which could occur due to parasitic causes.

The outputs from logic circuitry 200 are provided (1) at the collectors of transistor 220 (collector 220-1 provides the reset current to reset the oscillator following detection of a QRS signal); (2) on the line 203, which signal (IS) goes to a logic 1 following detection of a QRS signal and after stimulus is connected to the inhibit circuit 350 to inhibit delivery of a stimulus pulse following detection of a natural beat or any second stimulus pulse; (3) the hysteresis signal on line 252 which is connected to the rate determining circuit 250 and goes to a logic 1 when the pacer is in the inhibited mode; and (4) the logic signal generated at the output of gate 240 and connected to rate determining circuit 250 to switch the oscillator rate to the test rate (e.g., 95 bpm) when interference is detected. The signals at nodes 209, 210 are connected to program logic circuit 72.

Examining the detail of the circuitry, upon occurrence of a QRS signal which exceeds the threshold of amplifier 100, the input to gate 205 goes from logic level 0 to logic level 1. This signal is inverted through gates 205, 206 and 207 and applied through clock input gate 211 to the edge triggered flip-flop consisting of gate 212, gate pair 213, gate 215 and gate 216. Gate 243 is the reset gate for this flip flop. The QRS signal causes the output of gate 216 to go a logic 0, which in turn causes transistor 219 to conduct. When transistor 219 conducts, multiple collector transistor 220 conducts, providing a current at collectors 220-1, 2, 3. As is seen below in the discussion of the oscillator circuit 300, the current at collector 200-1 causes a very rapid time-out and consequent resetting of oscillator 300. Collector 220-3 of transistor 220 is tied to the base of transistor 225, such that that latter transistor is driven to conduction when transistor 220 conducts. The collector of transistor 225 may be used, as for a temporary pacer, to provide an output each time a QRS signal is detected. In the temporary pacer embodiment, a bulb with a current amplifier can be placed between the collector of transistor 225 and the source supply, to indicate when natural beats are inhibiting pacemaker operation. $I^2L$ gate 226 has one collector tied to its base, such that its other collector (tied to line 220-3) acts as a current sink of about 10 nA, in order to prevent transistor 225 from turning on except when a QRS is detected.

Upon resetting of the oscillator following either a QRS signal or a delivered pulse, the RI signal on line 204 goes low, producing a logic 1 at the collectors of gate 244. This logic 1 is connected to reset gate 243, producing a logic 1 at the output of gate 216. Thus, during the refractory period transistor 219 is held off, and detected signals cannot be passed through for resetting of the oscillator. After the end of the refractory interval, the RI signal goes high and the output from gate 244 sets flip-flop 237, providing a logic 0 signal on line 203 which is connected to the inhibit circuit.

Following delivery of a pulse from the output circuit, the line DP goes low, resetting flip-flop 235 and providing a logic 0 signal on line 252. As is seen in connection with the discussion of circuit 250, this effectively deactivates the hysteresis rate portion of circuit 250, such that the oscillator returns to normal rate operation.

Reverting back to the input node 163 to logic circuit 200, it is seen that gates 206 and 207 have collectors which are connected respectively to inputs of gates 241 and 242, which in turn have outputs connected to flip-flop gates 239 and 240 respectively. Gate 241 also has a wired-AND connection from gate 243 which represents the refractory signal (this is a logic 0 during the refractory interval and a logic 1 following the refractory interval). A collector of gate 244 is wired-AND connected to the input of gate 242, which collector is at a logic 1 during the refractory interval and a logic 0 after the refractory interval. Additionally, the QRS signal which is developed at the output of gate 215 (which goes to a logic 1 when the QRS is present, until flip-flop 215, 216 is reset) is inverted through gate 238 and connected to the input of gate 240. This combination of inputs to flip-flop 239, 240 causes it to switch to a logic 0 output when interference is present, but not when just a QRS signal is detected. This logic 0 output from gate 240 is connected to the rate selector circuitry 250, to cause the oscillator to operate at the test rate (95 bpm), as discussed below.

Reviewing the operation of this portion of the logic circuitry, it is noted that the wired-AND connection at the input of gate 241 requires the condition that the oscillator not be within the refractory interval and also that interference be present, in order to cause the output of gate 241 to switch to a logic 0, thus resetting flip-flop 239, 240 to provide a logic 0 output signal. Note that when there is interference and the oscillator is not within the refractory interval, both inputs to gate 241 are at a logic 1 level, such that the output from gate 240 is caused to be 0. However, if the interference signal comes through during the refractory interval, gate 241 is not switched and gate 240 holds the output of flip-flop 239, 240 at 1, such that the oscillator is prevented from switching to the test rate. If the flip-flop had previously been switched such that the oscillator was operating at the test rate (e.g., 95 bpm), and then a QRS was detected, the signal gated through gate 238 to the input of 240 causes the flip-flop to be reset such that the rate goes back to the normal operating rate as long as there is no interference present. Note also that if interference had been present and had stopped during the refractory interval, both inputs to gate 242 become a logic 1 level, such that again the flip-flop is reset.

There is thus provided a logic circuit which performs the following functions, utilizing I²L gate circuitry:

a. The oscillator is reset upon occurrence of detection of a natural QRS signal, but not by interference.

b. When interference is present at the end of the refractory interval, the oscillator switches to a test rate and remains there until the interference ceases and the oscillator is again in the refractory period.

c. Hysteresis logic signals are developed for switching the oscillator into and out of hysteresis rate depending upon whether the oscillator was last reset due to timing out or due to detection of a natural QRS signal.

RATE DETERMINATION CIRCUIT

The rate determination circuit 250, shown in FIG. 3, is designed to interface with the oscillator 300. The output of circuit 250, at node 201, is a current $I_R$, or rate current, which current controls the speed of switching of the oscillator, and thus its timing rate (as is described fully in connection with circuit 300 below). There are three inputs to the rate circuit, as follows:

1. A first input is provided by I²L gate 287 in accordance with external programming. Gate 287 is normally off, or non-conducting, such that its output is a logic 1. However, when it is desired to program a change to the test rate of 95 bpm, injector current is provided to this gate, such that its output goes to a logic 0 level.

2. Line 252 carries the hysteresis signal. It is normally at a logic 0 level, but goes to a logic 1 level when a QRS signal has been sensed and the pacer is acting in the inhibited mode. This signal reverts to a 0 level following delivery of a stimulus pulse.

3. The logic signal provided on line 248 is normally at a logic 1 level, but switches to a logic 0 level when interference is detected, thus causing the oscillator to operate at the test rate for the duration of the interference.

Examining the detail of circuit 250, transistors 266 and 267 are normally conducting, such that the current through them is adjustable by the size of resistance 265 connected between the emitter of transistor 267 and ground. Note that transistor 267 is held conducting by connecting its base to the injector rail. Transistor 266 is normally held conducting by the current from terminal 270-1 of transistor 270. Under normal operating conditions (stimulus pulses are being delivered), transistor 276 and diode 281 are not conducting, such that $I_R$ is determined solely by the value of resistor 265. The current on line 270-2 is shunted through line 252 into the output of flip-flop 235. However, if a QRS signal is detected, the signal on line 252 goes high, enabling an amount of current not consumed by the current sink of transistor 280 and resistor 260 to flow through diode 281. Since the collector current of transistor 267 is appreciably fixed by resistor 265, the increased current contribution through diode 281 means a reduced flow from transistor 266, which in turn means a reduction in $I_R$. Consequently, during the inhibited mode of operation, $I_R$ is reduced, which in turn results in lengthening the oscillator time-out period and causing a reduction in the oscillator rate to the lower hysteresis level. The value of resistance 260 is adjustable to set the effective rate, or escape interval during the inhibited mode of operation. The value of resistor 260 establishes the amount of current through transistor 280, and thus the current from collector 270-2 that is available to go through diode 281.

The test current ($I_{TEST}$) is derived from the combination of transistor 270 and resistance 255. The value of the test current can be adjusted by adjustment of resistor 255, and is nominally set to correspond to a rate of 95 bpm. Note that current generated by the combination of transistor 270 and resistor 255 will vary linearly with the supply voltage that is connected to resistance 255, such that monitoring of the test rate will give an indication of the status of the battery source. The base of transistor 270 is tied to the injector inputs of gates 268A and 268B, which injector inputs are not tied to the injector rail. This provides an effective voltage clamp of about 0.5 volts between the base of transistor 270 and ground, which is also connected between the base of of transistor 280 and ground. First collector 270-1 is connected to the base of transistors 284 and 266; collector 270-2 is connected to the collector of transistor 280; collector 270-3 is connected to the base of transistor 280, as well as fed back to the base of transistor 270; and collector 270-4 is connected to the bases of transistors 275, 276 which are connected in current mirror fashion. The collector current of transistor 276 is the test current, the collector being tied to node 201. Gates 285-291, seen at the bottom of the rate determining circuit, provide proper logic signals corresponding to the conditions when it is desired to operate the pacer at the test rate.

Under normal conditions, line 248 is at a logic level 1, and gate 287 is off, holding collector 270-1 at a logic level 1 and collector 270-4 at a logic level 0. Under these circumstances, transistor 276 is not conducting, but transistor 266 is conducting, providing the path for the normal $I_R$. Each of the four collectors of transistor 270 carries one-fourth of the current through resistor 255. Most of the current from collector 270-1 is shunted through transistor 284 and diode 282, thereby providing a 0.9 volt bias to the base of 266. The current of collector 270-4 is sinked into collectors of gates 290 and 288. When a logic 0 appears on line 248, or the presence of the external magnet causes gate 287 to be energized, producing a logic 0 at its output, collector 270-1 goes to a logic 0 level, thus turning off transistor 266, while the current through that collector is sinked into gates 291 and 289. At the same time, a logic 1 is placed on the bases of transistors 275 and 276, such that the collector of transistor 276 carries one-fourth of the current provided by the emitter of transistor 270. This test current then constitutes the entire $I_R$, since the normal conduction path through transistor 266 is open.

The rate determining circuit as shown illustrates circuit means for providing three different levels of rate current, namely the normal level (e.g., 70 bpm), the hysteresis level (60 bpm) and the test level (e.g., 95 bpm). All of these rates can be adjusted by adjusting respective resistors. In practice, additional levels may be provided under the control of a register in logic circuit 72 (or an equivalent means), which register in turn is set by external programming signals. As seen below in connection with the circuit of FIG. 9, the current source comprised of transistor 267 and resistor 265 may be replaced with a combination of current sources which can be controlled to give variable programmed levels of rate current, corresponding to varying pacer rates. Thus, the outputs of I²L gate sinks 610, 611, 612, 613, or of an equivalent arrangement, may be connected directly to the emitter of transistor 266 to provide programmed changes in the oscillator rate.

I²L OSCILLATOR

Referring now to FIG. 4, there is shown a circuit diagram of the oscillator 300 of this invention. Before examining the details of all of the components, attention is directed to linear transistors 320 and 330, which provide respective charging circuits to charge capacitor 345 from different directions. It is noted that the collector terminals of each of these multiple collector transistors are connected in different arrangements, and this will be seen to lead to different charging times for charging capacitor 345 in opposite directions, which in turn produces a predetermined duty cycle for the oscillator output pulse. This duty cycle, for the circuit illustrated, is chosen to provide a refractory interval which is 40% of the total oscillator period.

Transistors 320 and 330 are tied together in a current mirror configuration, such that the currents of each collector of each transistor are the same. These collector currents in turn are set by $I_R$, which is connected at node 201 from the rate determining circuit to the base of transistors 320 and 330. Two of the collectors of 320 are connected in a feedback loop to the base, and one collector of 330 is connected in a feedback loop to the base, such that each of the collectors carries a unit of current which is equal to one-third $I_R$. Note also that, except for the feedback path from the emitter of transistor 323 to the base of transistor 311, the two sides of the oscillator circuit are symmetrical, and operate in the same manner.

In normal free-running operation, without any reset from the detection of a QRS signal, the cycle is re-set when capacitor 345 charges to a switching point by $I_{left}$. After charging to this point, the circuit switches and the capacitor is then charged by the current designated $I_{right}$. The current $I_{left}$ is provided from 2 sources, namely collector 230-2 of transistor 320 and collector 330-1 of transistor 330. As noted, these 2 transistors are tied in a current mirror configuration, and are enabled by current $I_R$ (from the rate determining circuit) to provide a predetermined current at each collector terminal. When capacitor 345 is being charged by $I_{left}$, transistor 324 is not conducting, and transistor 334 is conducting. Also, since the stated condition is that there has been no QRS signal, there is no current from transistor 311. In these circumstances, the current from collector terminal 320-2, in the amount of 1 current unit, flows in the direction indicated by $I_{left}$. The current from collector 320-1 is shunted through conducting transistor 334, and does not affect capacitor 345. On the other hand, the current from collector 330-1 of transistor 330 is added to current $I_{left}$, providing 2 units of charging current. The current from collector 330-2 is shunted directly to ground through transistor 334.

With 2 units of charging current, capacitor 345 charges to about 0.9 v, at which point transistor 323 is caused to conduct. The current from transistor 323 exceeds the 20 nA sink capacity of gate 325 and switches on transistor 326, the output of which is connected to the input of gate 337 of the double set-reset flip-flop comprised of gates 327, 328, 337 and 338. Note that transistor 326 must be able to sink at least ½ of the injector current at gate 337 in order to initiate the switching operation which starts a new cycle. Upon switching, the output of gate 328 provides a logic 1, which in turn switches on transistor 324, immediately pulling its collector, and the left side of capacitor 345, essentially to ground. Just before switching, the right side of capacitor 345 had been at about 0 volts, due to the fact that transistor 334 was conducting. The abrupt change of voltage on the left side of capacitor 345, in the amount of about 0.9 v, is transferred to the right side, trying to cause it to go to about −0.9 v, but being clamped at about −0.5 v by the collector substrate diode of transistor 334, thereby providing a negative signal at node 348, the oscillator output. This in turn is connected to the emitter of transistor 351 of the inhibit circuit, enabling generation of an output pulse. It is also noted that at the same time that the output of gate 328 went to a logic 1 level, the output of gate 338 went to a logic 0 level, thereby turning off transistor 334 and completing switching of the left and right circuit portions of the oscillator.

Following this, with transistor 334 non-conducting and transistor 324 conducting, the operation of the oscillator circuit is reversed. When capacitor 345 charges to the switching value, transistor 333 turns on, thereby switching transistor 336 and resetting the double set-reset flip-flop, which in turn reverses the charging path. Note that when capacitor 345 charges from the right side the charging current has 2 components, from transistors 330 and 320 respectively. Transistor 330 provides a current from two collectors tied together, shown at 330-2, while transistor 320 provides current from one terminal as shown at collector 320-1. Thus, $I_{right}$ is comprised of three current units, as compared to $I_{left}$ which was comprised of two current units. Since the charging time is inverse with the charging current, capacitor 345 will charge to the switching value of about 0.9 v in ⅔ of the time that it took charging current $I_{left}$ to charge capacitor 345 to the switching value. Thus, a full period of the oscillator consists of a first portion which is 40% of the total period, during which the capacitor is charged by $I_{right}$, and a second portion which consists of 60% of the total time period, during which the capacitor is charged by $I_{left}$.

It is seen that the output of gate 328 provides a logic 1 during the shorter time period (corresponding to the refractory period) and a logic 0 for the rest of the period, such that it is representative of the refractory signal. The Refractory Inverse (RI) signal, which is the inverse of the output of gate 328, is taken from the output of gate 338 and connected to node 204 for use in the logic circuit.

The currents provided for driving transistors 324 and 334 respectively into conduction are provided by multiple collector transistor 340, which has a feedback collector connected to a current source 341, 342. Circuit 341 is made up of two I²L gates, each of which has one of its collectors tied to its base, such that the collector current appreciably equals the injector current. The other three collectors of each gate, being tied together, carry a current of three times the injector current. These collectors are coupled to the emitter of the NPN transistor 342 (which has its base connected to the injector rail), providing an efficient current source which is connected to the base of bipolar transistor 340. Care must be taken that the voltage drop between the injector rail and the emitter of transistor 342 is small enough to provide sufficient voltage drop across the gate 341. By coupling this current source to the feedback collector of transistor 340, and coupling the respective other collectors to the respective bases of transistors 324 and 334, sufficient current is provided to drive those transistors into conduction far enough to sink the amount of current that they have to take when conducting and switching.

As long as oscillator 300 is free-running, a negative output is provided at node 348 every time the capacitor is charged by $I_{left}$. It is to be observed that the duty cycle can be adjusted by adjusting the collector configurations of transistors 320 and 330. However, whatever the duty cycle the rate is set by the current provided from each collector of those 2 transistors, and this in turn is set by $I_R$. In practice, the oscillator duty cycle may be programmable by switching the collector arrangements with conventional logic circuitry. For example, if the pacemaker is programmed to operate above 125 bpm, it would then be desirable to adjust the duty cycle by changing the number of collectors from transistors 320 and 330 respectively which are connected to capacitor 345.

In the event that a QRS signal is detected, transistor 220 is driven to conduction, causing the current at collector 220-1 to flow into the base of transistor 311, thereby turning it on. The current delivered by transistor 311 is much greater than the normal $I_{left}$ current. Note that transistor 311 can only be turned on during the portion of the cycle when $I_{left}$ is charging capacitor 345, due to the refractory logic. The addition of the current from transistor 311 produces almost immediate chargeup of capacitor 345, and consequent switching and resetting of the oscillator. At the time of switching, a current is applied to the injector input of gate 312, turning it on. Gate 313 is connected to provide a 5 nA sink, which current passes through transistor 310. However, gate 312 provides an additional sink which permits greater current flow through transistor 310, thereby diverting current from the base of transistor 311. This feedback loop acts to stop the switching action quickly after it occurs, saving current and avoiding overshoot. Note that gate 312 does not switch before transistor 326 has switched, since the threshold for switching gate 312 is greater than for switching transistor 326. The $V_{be}$ of transistor 326 is less than the voltage drop across gate 312 at their switching point, illustrating the principle of utilizing differences in voltage drops of different devices in order to achieve a predetermined circuit operation.

INHIBIT CIRCUIT

Figure 5:
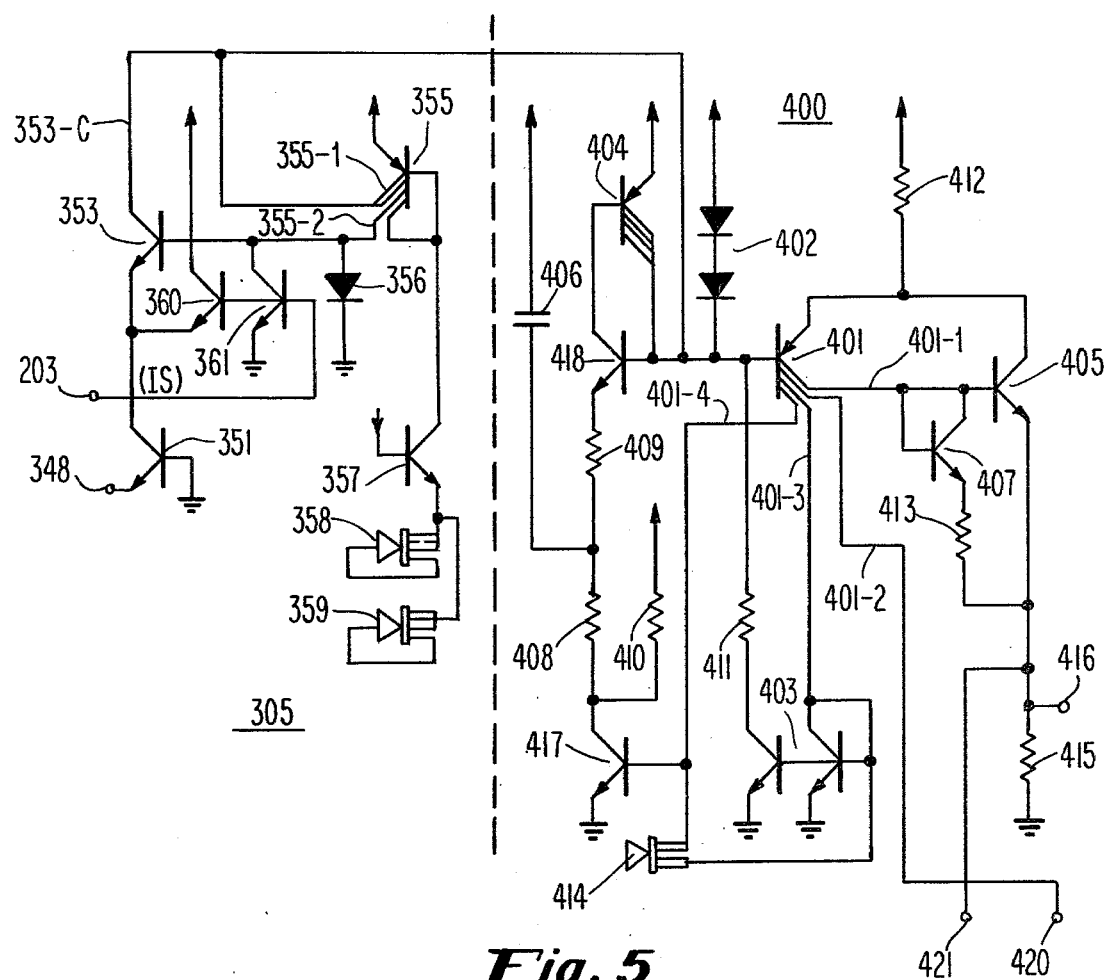
FIG. 5 is a circuit diagram of the inhibitor circuit (350) and pulse width circuit (400) of this invention.

Inhibit circuit 350, illustrated in FIG. 5, receives a negative-going input at node 348 whenever the oscillator is reset, and a positive-going inhibit signal (IS) at node 203 following detection of a QRS. The circuit provides a negative-going (or logic 0) output signal at collector 353-C of transistor 353 when a pulse is to be delivered, but this output signal stays high (at about V+) if the logic circuit delivers an inhibit signal to node 203.

The base of transistor 355, and one collector, are connected to a current sink comprised of $I^2L$ gates 358, 359 and transistor 357. This provides a relatively large sink current, thereby holding transistor 355 strongly on and normally maintaining collector 355-1 at about V+. Since this collector is tied to 353-C, that point also is normally held at a high level. Diode 356, connected to collector 355-2 and to the base of transistor 353, clamps that base to a voltage of about 0.5 volts.

In operation, when a negative going signal is received at node 348 from the oscillator, transistor 351 is turned on, providing a conduction path through transistors 351 and 353, thus sinking through collector 353-C a considerable amount of current. However, if the signal from the oscillator was produced by a QRS, transistor 361 is turned on, grounding the base of transistor 353 and preventing it from conducting. This permits collector 353-C to stay high (while current flows through transistors 360 and 351). Thus, an output signal is inhibited whenever the oscillator has been reset by a QRS. The relatively high current delfvered at collector 355-1 stabilizes the output, making it difficult for the pulse width circuit to be triggered by external or extraneous field signals.

PULSE WIDTH CIRCUIT

The pulse width circuit, shown as circuit 400 in FIG. 5, takes its output from collector 353-C of the inhibit circuit 350, and delivers a pulse of predetermined width at node 416, which is connected to the base of output transistor 451 in the output circuit. When the input is at the normally high state, or at about V+, plural collector transistor 401 is held non-conducting. Transistor 401 is a PNP transistor having its emitter connected through resistor 412 to V+. Collector 401-3 of transistor 401 is connected to current mirror circuit 403, which has an output connected through resistor 411 back to the base of transistor 401. Circuit 403 is normally held non-conducting by gate 414. This combination comprises a fast acting thyristor, in that when transistor 401 is turned on (by a negative signal) and current flows through collector 401-3, this causes current to flow through resistor 411 and the base of transistor 401, turning it on even harder. Thus, when a negative signal appears at the input to the pulse width circuit, the circuit turns on very quickly and sharply.

Prior to turn-on, the timing capacitor 406 is uncharged, a first side being connected directly to V+ and a second side being connected to V+ through resistors 410 and 408. However, when transistor 401 turns on, current is provided through collector 401-4 to the base of transistor 417 (normally held off by gate 414), thereby turning it on and providing a charge path including capacitor 406, resistor 408 and transistor 417. Since transistor 417 provides an effective short circuit, the charge time is determined by the RC combination of capacitor 406 and resistor 408. After a predetermined time period (the pulse width), the voltage at the junction between capacitor 406 and resistor 408 drops to a level sufficient to enable turn-on of transistor 418. Transistor 418 and transistor 404 comprise another thyristor combination, current flow through transistor 418 causing increased current flow through transistor 404, which turns on transistor 418 even harder. Consequently, very quickly the base of transistor 418, which is tied to the base of transistor 401, goes to approximately V+, thus blocking the current supply through the base of transistor 401 and turning it off. Following turnoff of transistor 401, transistor 417 is likewise turned off, and capacitor 406 discharges to its normal condition through resistor 409 and transistors 418 and 404 and also through resistors 408 and 410. Thus, the appearance of a negative going signal at the input to the pulse width circuit causes transistor 401 to be turned on for a precise time period determined by the RC time constant of capacitor 406 and 408, both the leading and trailing edge of the pulse being very sharp due to the 2 thyristor actions.

When transistor 401 is turned on, the current through each collector is stabilized to about 2 uA by the circuit connected to collector 401-1. This circuit comprises a transistor 407 with resistor 413 connected to its emitter, and transistor 405 which has its emitter connected to resistor 413 and its collector connected to resistor 412. The voltage across diodes 402, in combination with resistor 412, limits the current through transistor 405, which flows for the defined pulse width, to a stable value of about 100 uA. This current flows across resistor 415 tied between the emitter of transistor 405 and ground, and develops a signal at node 416 which turns on the output transistor of the output circuit, for delivery of the stimulus pulse. Circuit 400 is thus seen to provide a sharply defined pulse of a predetermined width and amplitude. The circuit is low current triggered and delivers a high constant output pulse substantially independent of source voltage. Nodes 420 and 421 provide connections to the high rate limiter circuit 425, as described 30 immediately below.

HIGH RATE LIMITER

Figure 6:
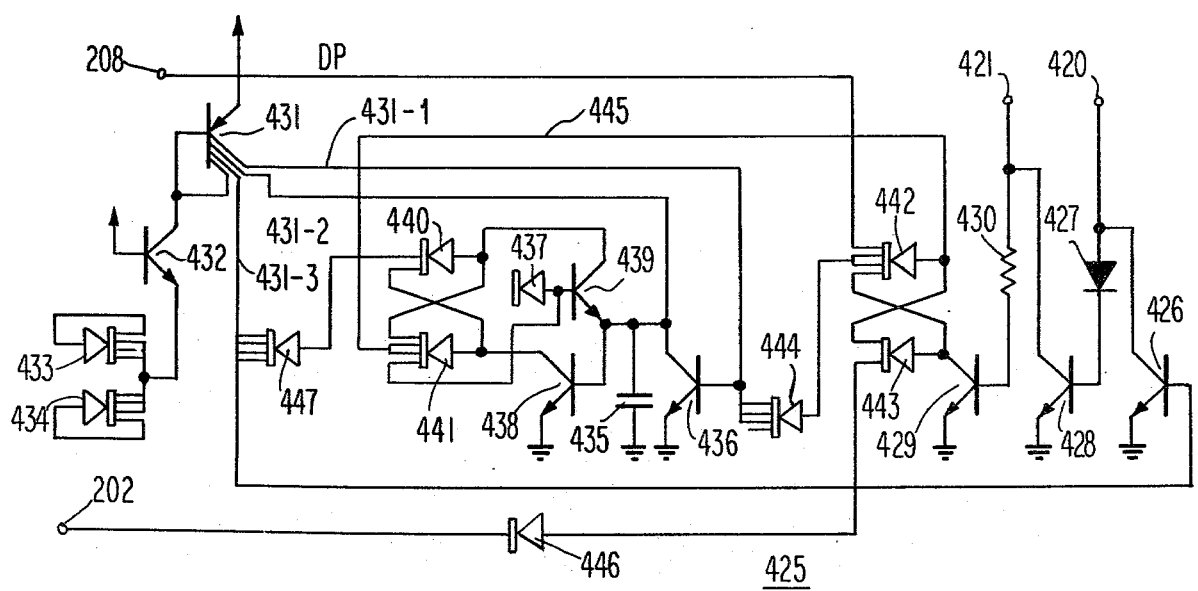
FIG. 6 is a circuit diagram of the high rate limiter (425) of this invention.

The high rate limiter circuit 425, shown in FIG. 6, is designed for limiting the rate at which pulses can be delivered from the pacer output to the heart. The input to this circuit is received at node 421 which is connected to node 416, the output of the pulse width circuit. This signal (positive-going when a pulse is delivered) is connected to the collector of normally off transistor 428 and to resistor 430, the other end of which resistor is connected to the base of transistor 429. In normal operation, the gate 447 at the far left of the circuit provides a logic 1 signal, which signal is connected to the base of transistor 426 at the far right of the diagram as illustrated, maintaining it in a conducting condition. As long as this situation holds, the current at node 420, coming from transistor 401 (in the pulse width circuit) during the output pulse, is shunted through transistor 426. This prevents current from going through diode 427 and keeps transistor 428 turned off during the time of the output pulse. However, if transistor 426 is turned off due to detection of a high rate, the current which is normally delivered to node 416 is instead shunted to ground through transistor 428, such that no output signal is developed at node 416. In the high rate limiting mode, delivery of stimulus pulses is continued, but at a rate below the high rate limit.

The timing of the high rate limiter is established by capacitor 435 and the current delivered from collector 431-2 of transistor 431. Transistor 431 has one of its collectors tied to its base and to the current sink made up of transistor 432 and gates 433, 434. As discussed in connection with the identical arrangement in other circuit portions of this invention, this establishes the maximum current flow in the other collectors, including the charging current on collector 431-2. Under normal conditions, capacitor 435 has been charged to a high level, thereby turning on transistor 438, causing a 0 logic level to be placed upon the input of gate 441. At the same time, this causes the output of gate 440 to be at a 0 level and the output of gate 447 a logic 1. The situation is maintained this way as long as the charge on capacitor 435 maintains transistor 438 conducting.

When a pulse appears at node 421, transistor 429 is turned on, causing switching of the flip-flop made of gates 442 and 443 to produce a 0 logic signal at the input to gate 444. At the same time, the signal on the line designated DP drops from a logic 1 to a logic 0. Gate 444 places a logic 1 on the base of transistor 436, driving it into conduction and causing discharge of capacitor 435 which in turn causes transistor 438 to be non-conducting. The discharge of capacitor 435 takes some milliseconds before through transistor 439 a logic 0 is placed on the input of gate 440, thereby setting the flip-flop 440/441. A logic 0 from output 441 now switches gate 442, thereby terminating the discharge period of capacitor 435. At the same time a logic 1 from gate 440 switches gate 447 thereby causing transistor 426 to be non-conducting. If the pulse-width at node 416 has not yet terminated as it would under normal conditions, transistor 428 will do so, enabled by current from node 420. Thus, the discharge-time of capacitor 435 provides a narrow window for the pulse at node 416 to activate the output stage. The recharge time of capacitor 435 depends upon its value. However, the important feature is that so long as the voltage on capacitor 435 has not recharged sufficiently to cause transistor 438 to again conduct, transistor 426 remains non-conducting, such that transistor 428 will shunt any pulse appearing at the output of the pulse width generator, thereby inhibiting delivery of another pulse. Immediately upon recharge of capacitor 435, the output of gate 447 again goes to a logic level 1, which effectively takes transistor 428 out of operation, restoring the condition that permits an output pulse to be delivered. Note also that the signal on line DP returns to a logic 1 level following termination of the pulse width signal. Thus, the signal on this line delivers a logic 0 pulse only when and as the pulse is actually delivered.

Gate 437 is connected to provide a source of about 10 nA. This is tied to the base of transistor 439, which has its collector connected to the input of gate 440, and its emitter to capacitor 435. In the absence of a pulse, transistor 439 does not conduct. Since the voltage at the input of gate 437 is about 0.5 v, and $V_{be}$ of transistor 439 is about 0.47 v, a 30 mv differential is used to detect discharge of 435, i.e., 439 does not conduct until the voltage across it drops to 0.030 volts. This drops the input to gate 440 to a logic 0, setting flip-flop 440-441 and causing switching at the output of gate 447. When capacitor 435 charges up to the point where 438 conducts, flip-flop 440-41 is reset. The feedback connection from the output of gate 441 to the base of transistor 439 prevents reverse current flow through that transistor at the time that flip-flop 440, 441 switches. Note also the line from gate 443 through inverter 446 to node 202 of the logic circuit, which delivers a signal to the logic circuit to prevent double triggering of the pulse width circuit by the rate oscillator.

OUTPUT CIRCUIT

Figure 8:
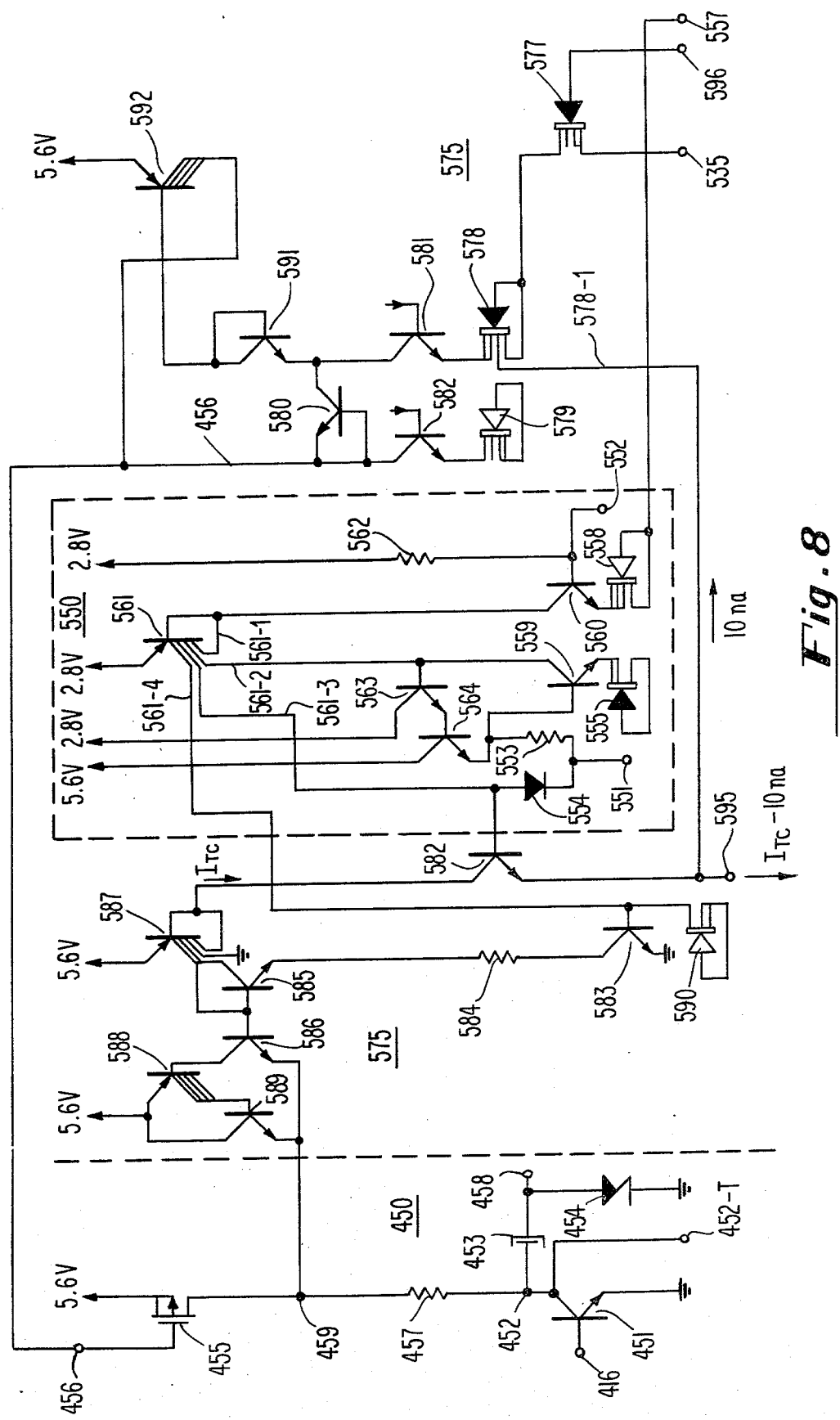
FIG. 8 is a circuit diagram of the injector rail circuit (550) and the threshold test control circuit (575) of this invention.

The output circuit is shown as circuit portion 450 in FIG. 8. As discussed previously, detection of a QRS signal or timeout of the oscillator causes a positive going signal to appear at node 416, driving transistor 451 into conduction. This permits the discharge of capacitor 453 through transistor 451, producing a negative stimulus pulse which is delivered to the heart from output node 458. Zener diode 454 is used for the conventional purpose of defibrilation protection of the electronics. Between pulses, capacitor 453 is charged through FET 455 and resistor 457. FET 455 is maintained in a normally conductive state by holding line 456 at a normally negative level with respect to the supply value. However, during the threshold testing mode of operation, line 456 goes toward +5.6 v such that FET 455 goes to a non-conducting state. As discussed hereinbelow, during testing voltages of programmed values are introduced from circuit 575 (Threshold Pulse Level Control Circuit) at node 459 for charging capacitor 453. By controlling the voltage supplied to capacitor 453, output pulses of different incremental values are obtained for purposes of testing. Node 452-T is tied to the Marker Generator and Test Current Source circuit 500.

MARKER GENERATOR AND TEST CURRENT SOURCE

Figure 7:
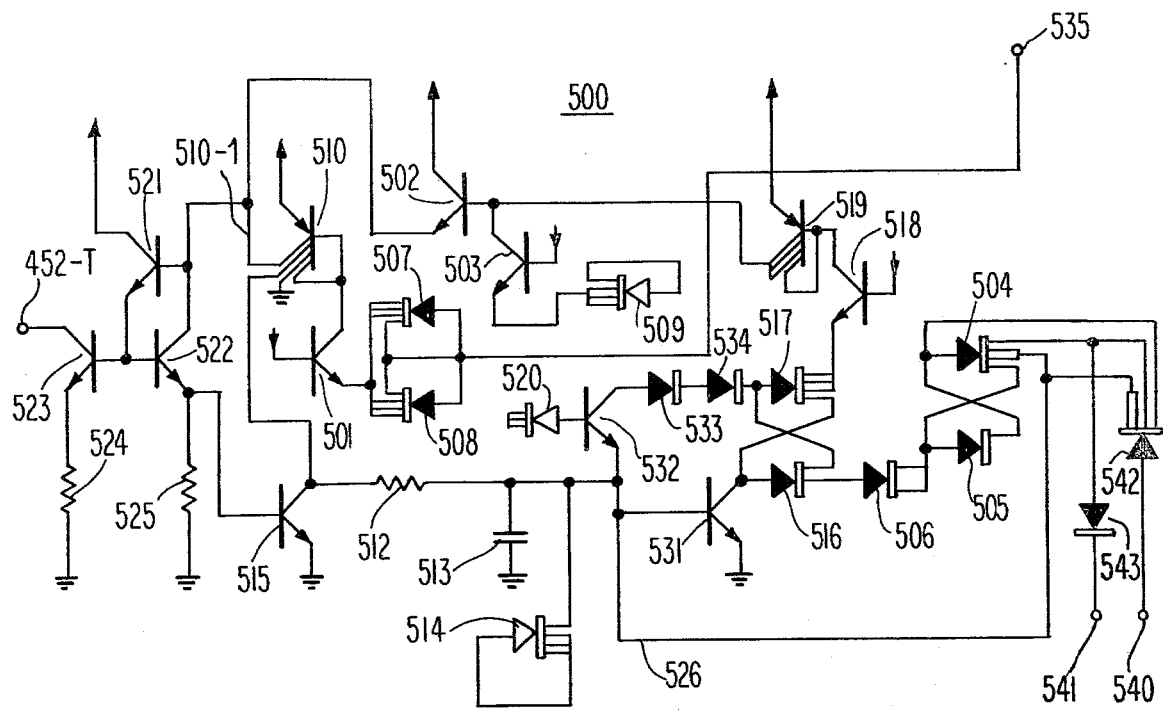
FIG. 7 is a circuit diagram of the marker generator (500) of this invention.

The marker generator and test current source circuit 500 is shown in FIG. 7. The purpose of this circuit is twofold. First, when the pacer goes into the test mode, following decoding of a properly coded external signal, the circuit provides a 3 uA current at node 452-T, which current is utilized in generating the programmed threshold testing sequence of pulses. Additionally, shortly after the start of the test, the circuit provides, again at node 452-T, a 1 mA current-limited marker pulse having a pulse duration of approximately 2 ms. This pulse is, in the illustrated circuit, generated 50 ms following the last pacer pulse signal which activates the program "key" and enables start of the test. Generation of such a standard 1 mA marker pulse permits the physician to readily see when the test is starting by simply watching an ECG trace. As will be understood more fully in connection with the discussion of operation of the threshold pulse level control circuit, the marker pulse enables the physician to determine with certainty when to start counting the test pulses, so as to determine the patient threshold level. Alternately, the marker can be used for other purposes, such as signalling that a proper program has been received. The time delay of 50 ms is chosen in order to ensure that no pulse is delivered at about the time of the T wave. The marker generator pulse also has the advantage that it will be picked up as part of any ECG recording, so that at any later study of the ECG signal the start of the test will be clearly marked. Alternately, the marker pulse may be generated about 400 ms after the prior pulse, and connected to reset the oscillator. This recycles the pacemaker like a QRS and a rhythm gap on the ECG trace shows clearly where the test begins.

There are two inputs to circuit 500. A first input is received from the logic circuit at node 540. Under normal operating conditions, i.e., not in the test mode, this input is a logic 1 level, but it is switched to a logic 0 level at the start of the threshold test. Likewise, before the start of the threshold test a logic 0 signal is placed on node 535. As is seen in the description to follow, the signal at node 535 causes a 3 uA current to flow at the output node 452-T. The signal inputted at 540 causes the circuit to pass through a cycle which generates a 1 mA marker signal at node 452-T. The signal at output node 541 is connected to the logic circuit in the preferred embodiment.

In operation, when the external program is received with the proper key, the signal at node 535 goes to a logic 1 level. This places a logic 1 at the input to gates 507 and 508. These gates, in combination with linear transistor 501 provide a current source which is connected to the base and one collector of transistor 510. Before the test started, transistor 510 had been in a non-conducting condition, since no current could be sinked through transistor 501 into gates 507, 508. However, when the test starts, 501 conducts and consequently transistor 510 is placed in the conducting state. The resulting current flow through collector 510-1, which is fixed by the state of gates 507 and 508, is sufficient to turn on transistor 521, which in turn turns on transistors 523 and 522. The conduction path through transistors 521 and 522 and trim resistor 525 produces a base voltage on transistor 523, adjusted to sink desired 3 uA from the output at node 452-T.

At the start of the test, capacitor 513 carries essentially no voltage, since any charging leakage current which could be received by it is sinked into gate 514. However, when the test is initiated a logic 1 is placed on line 526, enabling the charging of capacitor 513 from transistor 510 through resistor 512. Capacitor 513 charges with a time constant determined by the current from transistor 510, which time constant is suitably approximately 50 ms. When the voltage across capacitor 513 rises to a sufficient value, transistor 531 is caused to conduct, setting the flip-flop consisting of gates 516 and 517, so that gate 517 provides a 0 logic output. This causes transistor 518 to conduct, which in turn permits transistor 519 to conduct. The high current output of the three common collectors of transistor 519 is connected to the base of transistor 502. Also connected to the base of transistor 502 is a current source comprised of transistor 503 with its emitter connected to gate 509. This provides a current sink which diverts current from the base of 502 and prevents spurious signals from being gated through transistor 502 and turning on the output circuit, thus erroneously triggering the pacer. Transistor 502 conducts only when the current from transistor 519 is greater than about 20 nA, the sink value of 503, 509. This sink circuit also provides for a quick turnoff after the marker pulse. When transistor 502 is turned on, additional current is provided into the base of transistor 521, driving it more heavily into conduction and causing transistor 523 to conduct a greater amount of current. In the preferred embodiment, the common base of transistors 523 and 522 is held at about 1 volt, stabilized by the base to emitter voltage of transistors 522 and 515. By adjusting resistor 524 appropriately, a 1 mA signal, ±20%, is achieved. This pulse lasts for about 2 ms, after which the circuit resets itself and the current at node 425-T returns to its normal constant value of 3 uA for the remainder of the test.

The marker generator circuit is reset in the following way. The increased current from transistor 502 also causes increased conduction of transistor 522, to the point where transistor 515 is turned on. This provides a discharge path for capacitor 513 through resistor 512 and transistor 515, which discharge time constant is determined by the values of resistor 512 and capacitor 513. When the value of the voltage on capacitor 513 drops to the point where transistor 532 starts to conduct, the entire circuit is reset and enabled for the next test. The output of gate 517 is then switched back to a 1 level, thus turning off transistors 518 and 519. The output of gate 516 is inverted through gate 506 and applied to flip-flop 504, 505, which is reset to prime the circuit for another cycle. Note that gate 520, which has its collectors open, provides a 10 nA current which is inputted to the base of transistor 532 when the base of 531 returns toward a 0 level, permitting current flow through gates 533 and 534 to quickly reset flip-flop 516, 517 at the end of the marker pulse. The voltage drop across gate 520 is about 30 mv greater than the $V_{be}$ of transistor 532, so that when C513 discharges to about 30 mv transistor 532 is caused to conduct. Thus, the difference in voltage characteristics of 520 and 532 is utilized to detect when capacitor 513 has discharged.

INJECTOR RAIL AND THRESHOLD PULSE CONTROL CIRCUITS

Referring again to FIG. 8, the injector rail circuit 550 is seen positioned within the threshold level control circuit 575. The injector rail circuit provides an output at node 552 for the white $I^2L$ cells, being the cells which are continuously on. It also provides an output at node 551, which is the injector rail for the black cells, and which is turned on only when the external signal is received. A second injector rail is needed, since the first injector rail is designed to provide the proper injector current for the white cells alone. If the black cells, when energized, were to be supplied from the same injector rail, the total load would change, and the injector current applied to the white cells would change. It is desirable to provide a second injector rail having the same characteristics as the first injector rail. The injector rail circuits could be duplicated, but a stand-alone injector rail circuit requires using a thick film high resistor, which must be an external resistor. In designing a circuit for a monolithic chip, it is highly desirable to provide a second injector rail circuit which does not require using another high resistor. For this reason, the injector rail circuit for the black cells has been designed as a current follower circuit relative to the first injector rail circuit, so that it automatically assumes the same characteristics.

The first injector rail is generated at node 552, where the voltage supplied is constantly available. This rail is provided simply by connecting high resistance 562 to the V+ power power supply. In the absence of an external magnetic signal, line 557 carries a logic 0, such that no current is sinked through gate 558 and transistor 560 is held non-conducting. However, when an external signal is present, line 557 goes to logic 1, and gate 558 switches to provide a logic 0 at its output, turning on transistor 560. The collector of transistor 560 is connected to the base of transistor 561, which base is connected in a feedback loop to first collector 561-1. A second collector, 561-2, is connected to the collector of transistor 559, having an emitter connected to current sink 555 which is arranged similarly to gate 558. Collector 561-2 is also connected to the base of transistor 563, which has its emitter connected to the base of transistor 564. The emitter of transistor 564 is connected to the base of transistor 559, and through current limiting resistor 553 to injector rail output 551. Collector 561-3 is connected to the base of transistor 582, and collector 561-4 is connected to the base of transistor 583, the latter two transistors being utilized in the threshold level control circuit.

In operation, when the magnet signal is present, gate 555 is energized, and acts as a current sink. It is able to sink an amount of current which is dependent upon the voltage level of node 551. The combination of gate 555 and transistor 559 provides a current match to the combination of gate 558 and 560, and transistor 561 is connected to match the current at collectors 561-2 and 561-1. Thus, the current through transistor 559 follows the current through 560 when the injector rail voltage at node 551 matches that at 552, and this is the condition in which the circuit stabilizes. Note that the feedback path from the base of transistor 563 through transistor 564 to the base of transistor 559 acts to stabilize this circuit to the point where essentially all the current from collector 561-2 is sinked into gate 555, which condition occurs only when the injector rails are matched.

Referring to circuit 575 of FIG. 8, when the proper external magnetic signal has been entered such that the test can commence, node 596 receives a logic 0 signal from the logic circuit, causing a logic 1 signal to appear at the output of gate 577. This provides the logic 1 signal at node 535, for use in the marker generator. Also, this causes a sink current to appear at the output of gate 578, thereby turning on transistor 581. Gate 578 in combination with transistor 581 provides a current sink of about 20 nA, and collector 578-1 is a current sink of about 10 nA (used in generating the threshold test current). When transistor 581 turns on, transistor 591 and 592 are also energized. Transistor 592 provides a current of about 20 nA, which holds node 456 (at FET 455) at about V+ minus 0.5 volts, which effectively turns off FET 455 and disables the normal output circuit path. Gate 579 in combination with transistor 582 provides a sink of about 5 nA, the remainder of the current from transistor 592 being shunted through transistor 580 connected between line 456 and the collector of transistor 581. This feedback holds the collector current of transistor 592 at about 20 nA, which is the desired level for holding FET 455 in an OFF condition.

Thus, following the delay between the time that the magnet signal is first sensed and the time that the key is properly entered, the output circuit is modified by taking FET 455 out of conduction. After this, the output circuit voltage is provided under control of transistor 587, which in turn is controlled by the threshold test current ($I_{TC}$). This test current is controlled by the logic circuitry, as is discussed more fully hereinafter.

When transistor 561 of the injector rail circuit is turned on, in the presence of an external magnetic signal, the current flowing at collector 561-3 turns on transistor 582, which then conducts current $I_{TC}$. The current at collector 561-4 turns on transistor 583, the collector of which is connected through resistor 584 to the emitter of transistor 585. Note that gate 590 provides a current sink connected to the base of 583, which keeps the base of that transistor normally off, and prevents it from floating. Note also that node 595, at the emitter of transistor 582, is clamped during the test procedure to approximately 0.5 volts by diode 554 which is connected between the base of transistor 582 and injector rail node 551. This clamp is utilized in controlling the voltage on the output of circuit 600 which establishes the different levels of threshold test current, as discussed hereinbelow.

In operation, when a given test current is conducted through transistor 582, this establishes the currents flowing in the collectors of transistor 587. Since transistors 585 and 586 are connected in a voltage follower configuration, the test current likewise controls the collector current of transistor 588 and the current supplied by transistor 589. Also, since the test current controls the current that flows through transistor 585, and thus across resistor 584, it controls the voltage appearing at the emitter of transistor 585. Due to the emitter follower arrangement of transistors 585, 586, the test current is seen to control the voltage that is developed at node 459. By this means, the programmed test current is caused to control the charging of capacitor 453, and thus the voltage level of the output pulses during the threshold test. Also, as was discussed in connection with the circuit 500, a constant current of about 3 uA is drawn at node 452-T during the test. This current enables discharge of capacitor 453 by a 0.5 volt increment during each delivered stimulus pulse, so that the capacitor is able to drop by this increment whenever the test program calls for a reduction in output level by that amount. This 3 uA also lowers the output impedance at node 459 by keeping transistors 589 and 586 conducting. Lowering the impedance of node 458 reduces the chance of interference and T wave sensing during the threshold test.

DIGITAL TO ANALOG CONVERTER CIRCUIT 600

Figure 9:
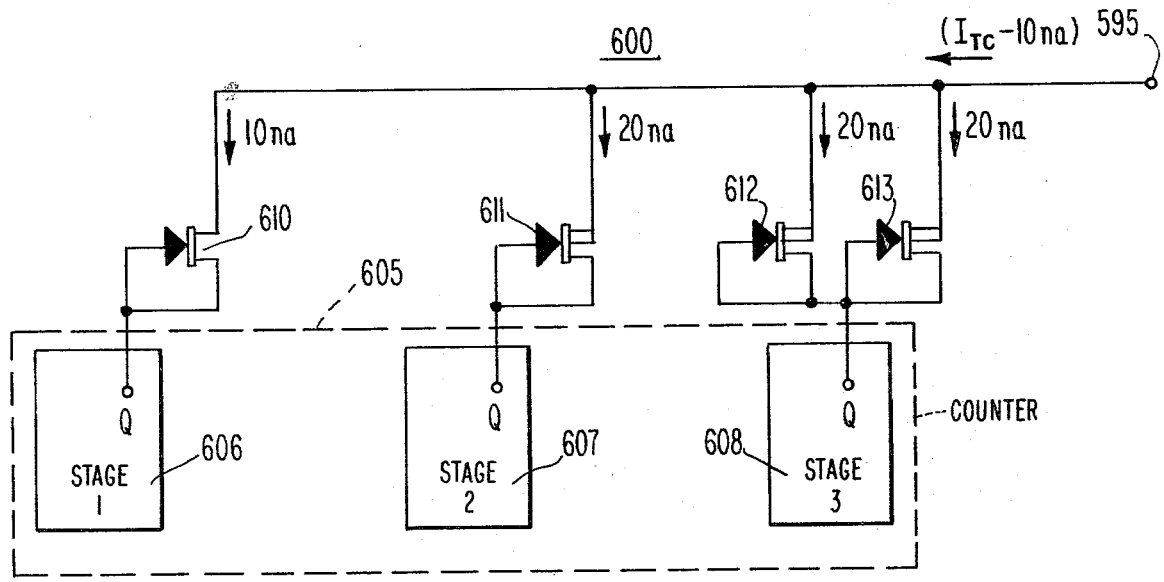
FIG. 9 is a circuit diagram of the digital to analog arrangement used in connection with the programmed threshold test of this invention.

The circuit 600 is shown in FIG. 9. Dashed block 605 is a diagrammatic representation of a three stage counter. The interconnections of the stages, and means for shifting data into the counter are not shown, these being well known in the art. Reference is made to U.S. Pat. No. 4,124,031 assigned to Vitatron Medical B.V., which discloses in detail a pacemaker having logic means for loading a counter in accordance with received programming signals. The counter and associated logic are, for the illustrated embodiment, made up of I$^2$L gates.

The key building block of the circuit 600 is the I$^2$L gate that has one collector tied back to its base. For the injector rail utilized, the feedback collector sinks 10 nA when the gate base is at a logic 1 level, but sinks no current when the gate base is held at a logic 0 level (in which condition the injector current is shunted away from the gate base). Consequently, each output collector of the gate acts as a 10 nA (1 current unit) sink when the gate input is 1. By utilizing different output collector combinations, and tying plural gate outputs in parallel, a programmable current sink of a variable current unit level is obtained.

For the embodiment illustrated, counter 605 has three stages. The Q output of stage 606 is connected to and controls the input of gate 610. Gate 610 has a single collector tied to common point 595, and can sink 0 or 10 nA. The Q output of the second stage 607 is connected to the input of gate 611, which has two collectors connected to point 595, and thus can sink 0 or 20 nA. The third stage 608 has its Q output connected to the inputs of two I$^2$L gates (612, 613), each of which have two output collectors tied to point 595. Thus, when the Q output of stage 608 goes high, 40 nA from point 595 are sinked into the combination of gates 612, 613. In addition to these programmable gate sinks, gate 578 (which is part of the theshold circuit) is a constant 10 nA sink during the threshold test, causing a steady 10 nA to flow through transistor 582. The counter-controlled gates provide for another 70 nA, in increments of 10 nA, such that $I_{TC}$ can be controlled to any level from 10 to 80. The following table shows the correlation between the current through transistor 582 ($I_{TC}$) and the count of counter 605. Note that each increment of 10 nA results in an increment of 0.5 volts in the delivered output pulse.

| THRESHOLD CURRENT | COUNTER SETTING | OUTPUT PULSE VOLTAGE LEVEL |
|---|---|---|
| 80 | 111 | 4 |
| 70 | 011 | 3.5 |
| 60 | 101 | 3 |
| 50 | 001 | 2.5 |
| 40 | 110 | 2 |

-continued

| THRESHOLD CURRENT | COUNTER SETTING | OUTPUT PULSE VOLTAGE LEVEL |
|---|---|---|
| 30 | 010 | 1.5 |
| 20 | 100 | 1 |
| 10 | 000 | .5 |

In practice, as disclosed in referenced U.S. Pat. No. 4,124,031, the initiation of a threshold test by a proper external program signal causes the counter to cycle from the highest level to the lowest, holding each counter setting for 4 delivered pulses. Thus, the physician can count the pulses following the marker pulse and determine the output voltage level at which capture is lost. The test is then terminated following which the output returns to its normal level.

We claim:

1. A pacemaker having means for providing stimulas pulses, and means for adjusting the rate of delivery of said stimulus pulses to one of a plurality of operating rates, characterized by comprising a controllable current generator and a current controlled oscillator, the oscillator having means for generating stimulus timing signals and connected to said current generator to operate at a rate determined by the current provided by said current generator, means for controlling said current generator to provide a control current at one of a predetermined plurality of levels, said oscillator having current responsive means for establishing the rate of said timing signals and multiple collector transistors in current mirror configuration, and a connecting circuit connecting said current generator to said oscillator so that said control current controls the current of said current responsive means, thereby controlling the rate of said stimulus pulses.

2. The pacemaker as described in claim 1, wherein said current generator circuit comprises means for adjusting the rate current in response to receipt of an external programming signal.

3. The pacemaker as described in claim 2, wherein said current generator circuit comprises means for generating control currents corresponding to pacing rate and hysteresis rate.

4. The pacemaker as described in claim 1, wherein said current generator circuit comprises a plurality of controllable current generators and switching means for switching each of said current generators into and out of connection with the output of said current generator circuit.

5. A pacemaker for generating and delivering pacing signals adapted for pacing a patient's heart, having an oscillator for generating timing signals for controlling the rate of delivery of said pacing signals, and having output circuit means connected to said oscillator for generating said pacing signals from said timing signals, and electrode connection means for connecting said pacing signals to said patient's heart, characterized by said oscillator comprising a current source for delivering a rate control current, a pair of multiple collector transistors in current mirror configuration, each of said transistors being connected to receive said rate current so as to control the current output from the collectors of each, a charging circuit having first and second charging paths, charge path means for alternately connecting a first set of collectors from said transistors to charge said charging circuit in said first path and for connecting a second set of collectors from said pair of transistors to charge said charging circuit in said second path so that said charging circuit charges alternately in one direction and then the other, and means for developing said timing signals as a function of said alternating charging.

6. The pacemaker as described in claim 5, wherein said switching means comprises a flip-flop connected to said charge path circuit so that it switches said charging paths each time said charging circuit charges to a predetermined value.

7. The pacemaker as described in claim 6, wherein said switching control means comprises a current source for controlling the switching levels of said switching control means.

8. A pacemaker adapted for delivering pacing signals to a human patient, having a stimulus circuit for generating pacing signals, an output circuit for delivering said pacing signals, a control circuit for controlling at least one parameter of said pacing signals, and means for receiving an external signal, characterized by said circuits comprising first and second groups of $I^2L$ gates, said pacemaker further comprising an injector current circuit having a first injector rail connected to said first group to provide injector current to the $I^2L$ gates of said first group and at least a second normally deenergized injector rail connected to said second group to provide injector current to the $I^2L$ gates of said second group when it is energized, and means for energizing said second injector rail upon receipt of an external signal.

9. The pacemaker as described in claim 8, wherein said energizing means comprises means for connecting said second injector rail to said first injector rail so that plural injector rails are provided which provide substantially the same injector current to the $I^2L$ gates of each of said first and second groups of $I^2L$ gates when said second injector rail is energized.

10. A pacemaker adapted for use in a human patient, having means for delivering pacing pulses, characterized by having means for controlling the rate of said pacing pulses, said rate controlling means comprising (a) a current source having a series combination of an $I^2L$ gate and linear transistor and an injector current circuit means connected to said $I^2L$ gate for controlling the current of said current source, and (b) means for utilizing said current source to control said pacing pulse rate.

11. The pacemaker as described in claim 10, wherein said pacemaker has a plurality of additional operating parameters, and means for controlling each of said additional operating parameters, each said means for controlling comprising a respective said current source to provide a respective parameter control current.

12. The pacemaker as described in claim 10, wherein said combination comprises an $I^2L$ gate having a feedback from output to input in combination with a multiple collector linear transistor.

13. The pacemaker as described in claim 10, comprising means for testing for pacer threshold, said testing means including current control means for providing a variable control current and means for controlling the output level of said pacing signals as a function of said variable control current, said control current means comprising a plurality of current source circuits.

14. The pacemaker as described in claim 10, wherein said first value is limited to about 10 na.

15. The pacemaker as described in claim 10, wherein said current source comprises said $I^2L$ gate having at least one output collector in a feedback connection to its input and at least one other output collector connected in series to said linear transistor, and a multiple collector linear transistor connected in series with said linear transistor, one output collector of said multiple collector transistor being connected in a feedback connection to the input of said multiple collector transistor and to said linear transistor, whereby the other output collectors of said multiple collector transistor are available as current sources.

16. The pacemaker as described in claim 15, wherein said multiple connector transistor has n said other output collectors connected in common, thereby providing a current source of n times said first value.

17. A pacemaker adapted for use with a human patient, having a plurality of operating parameters, characterized by comprising a plurality of current sources, each having an $I^2L$ gate with a feedback loop from output to input, and each having at least another output collector connected to a linear transistor, and means for controlling said parameters with respective different ones of said current sources.

18. A pacemaker having means for generating pacing pulses at its output, said pacemaker further having means for receiving an externally generated programming signal, characterized by having means responsive to receipt of said programming signal for generating at said output a sole marker pulse of a predetermined form, said marker pulse being in addition to said pacing pulses.

19. The pacemaker as described in claim 18, wherein said generating means generates said marker pulse a predetermined time interval following receipt of said programming signal.

20. The pacemaker as described in claim 18, wherein said generating means generates said marker pulse in a predetermined time relationship with the last preceding pacing pulse.

21. The pacemaker as described in claim 20, wherein said generating means has timing means to provide that said marker pulse follows said preceding pacing pulse by a time period of at least 50 milliseconds and less than 200 milliseconds.

22. The pacemaker as described in claim 20, wherein said generating means has timing means to provide that said marker pulse follows said preceding pulse by at least a predetermined refractory interval.

23. The pacemaker as described in claim 22, comprising means for resetting said pacing pulse generating means with said marker pulse.

* * * * *